(12) United States Patent
Melnik

(10) Patent No.: US 8,862,208 B2
(45) Date of Patent: Oct. 14, 2014

(54) SYSTEM AND METHOD FOR NONINVASIVE TISSUE EXAMINATION

(75) Inventor: Boris Melnik, Netivot (IL)

(73) Assignee: Medespel Ltd, Netivot (IL)

( * ) Notice: Subject to any disclaimer, the term of this patent is extended or adjusted under 35 U.S.C. 154(b) by 240 days.

(21) Appl. No.: 13/502,650

(22) PCT Filed: Oct. 21, 2010

(86) PCT No.: PCT/IL2010/000869
§ 371 (c)(1),
(2), (4) Date: Apr. 18, 2012

(87) PCT Pub. No.: WO2011/048596
PCT Pub. Date: Apr. 28, 2011

(65) Prior Publication Data
US 2012/0203115 A1     Aug. 9, 2012

Related U.S. Application Data

(60) Provisional application No. 61/279,517, filed on Oct. 23, 2009.

(51) Int. Cl.
*A61B 5/00* (2006.01)
*G06T 7/00* (2006.01)

(52) U.S. Cl.
CPC .............. *A61B 5/0059* (2013.01); *G06T 7/0012* (2013.01); *G06T 2207/30088* (2013.01); *A61B 5/443* (2013.01); *A61B 5/0075* (2013.01); *A61B 5/0064* (2013.01); *A61B 5/444* (2013.01); *A61B 5/445* (2013.01)
USPC ........................................................ 600/476

(58) Field of Classification Search
USPC ........................................................ 600/476
See application file for complete search history.

(56) References Cited

U.S. PATENT DOCUMENTS

| | | | |
|---|---|---|---|
| 6,069,689 A | | 5/2000 | Zeng et al. |
| 6,081,612 A | * | 6/2000 | Gutkowicz-Krusin et al. ............. 382/128 |
| 6,208,749 B1 | * | 3/2001 | Gutkowicz-Krusin et al. ............. 382/128 |
| 7,217,266 B2 | * | 5/2007 | Anderson et al. ............. 606/12 |
| 7,280,866 B1 | | 10/2007 | McIntosh et al. |
| 7,428,048 B1 | | 9/2008 | Farkas et al. |
| 7,967,016 B2 | * | 6/2011 | Anderson et al. ............. 128/898 |

(Continued)

FOREIGN PATENT DOCUMENTS

| | | |
|---|---|---|
| WO | WO 97/17013 A1 | 5/1997 |
| WO | WO 98/46133 A1 | 10/1998 |
| WO | WO 01/24699 A2 | 4/2001 |

*Primary Examiner* — Long V. Le
*Assistant Examiner* — Angela M Hoffa
(74) *Attorney, Agent, or Firm* — Oliff PLC

(57) ABSTRACT

A processing utility analyzes first measured data including at least two measured data pieces from at least two first spaced-apart measurement locations respectively within a first sub-region of the region of interest, and determines for each of the first locations a deviation parameter corresponding to deviation of the measured data piece from the reference response. The processing utility determines, for each of at least two of the measured data pieces of the first measured data, a relation between the deviation parameter and a predetermined threshold value corresponding to a condition of the predetermined abnormality, and generate a corresponding control signal and communicate it to the measurement unit. The control signal is indicative of a first scan direction towards at least one second location to be measured in the region of interest where a degree of the predetermined abnormality is higher than in the at least two first locations.

21 Claims, 12 Drawing Sheets

(56) References Cited

U.S. PATENT DOCUMENTS 8,326,404 B2 * 12/2012 Zeng et al. .................... 600/475
2007/0064985 A1 3/2007 Chhibber et al.
2011/0286643 A1 * 11/2011 Kislal .......................... 382/128
2011/0319877 A1 * 12/2011 Anderson et al. ............... 606/10

* cited by examiner

SYSTEM AND METHOD FOR NONINVASIVE TISSUE EXAMINATION

FIELD OF THE INVENTION

This invention is generally in the field of medical devices, and relates to a system and method for use in noninvasive tissue examination, in particular for detecting diseases/abnormalities in skin lesions.

BACKGROUND OF THE INVENTION

Skin examination by physicians is a widely used procedure aimed at timely determining various abnormalities on a patient's skin, in order to identify a skin disease or timely detect a condition indicative of possible development of a disease. For example, melanoma is a highly malignant tumor that starts when melanocytes produce black to yellow pigments color in normal skin or moles (nevus). Melanoma has doubled in incidence in recent decades and is increasing more rapidly than any other cancer. Melanoma metastasizes rapidly and widely. Early detection of a skin lesion as melanoma is a key factor in improving patient survival and decreasing treatment costs. About 3 million moles are evaluated by biopsy each year in the United States, and of those over 60,000 are diagnosed as melanoma that end in more than 8,000 deaths.

A number of optical techniques for identifying abnormal tissues and prevent unnecessary biopsies have been recently developed. Some of these optical techniques make use of multispectral digital dermatoscopy. According to these techniques, quantitative data are generated with sequences of images of skin lesions taken at different wavelengths of incident light. Image processing can be used by a clinician to decide whether the lesion should be biopsied or not. More specifically, the known used technologies include MoleMate and MelaFind techniques. The SIAscope MoleMate is a chromophore imaging system that probes 1 cm$^2$ to 2 cm$^2$ areas of skin using wavelengths of 400 nm to 1000 nm. Spectrally-filtered images are obtained and respective data is processed to determine the micro-architecture of the skin. SIAscopy measures the amount of collagen, hemoglobin, melanin, and melanin distribution in the epidermis and dermis. This information is presented in the form of maps called SIAscans, which are then interpreted by the clinician. MoleMate incorporates SIAscopy in a diagnostic algorithm specifically developed for use by primary care physicians. As with conventional dermatoscopy, diagnostic accuracy of the SIAscope depends on the experience of the physician interpreting the SIAscans. In addition, hyperkeratosis in seborrheic keratoses can be interpreted as dermal melanin, giving false positive results. MelaFind acquires 10 images for lesions that encompass the visible and near-infrared spectrum. Six scores are generated for each lesion based on constrained linear classifiers, with each classifier trained to differentiate melanoma from other pigmented lesions. A lesion is then recommended for biopsy if all six scores are above the threshold value. MelaFind has low specificity for melanoma detection.

Multiwavelength ultraviolet-visible spectrophotometry is a powerful tool for the characterization of biological tissues. With the acquisition of a spectrum of blood cells, it is possible to obtain information on parameters such as reflectance property, metabolism and chemical composition. Application of this technology coupled with spectral interpretation using the theory of light scattering allows for the analysis of cells. The method is known as particularly useful in the examination of reflectance properties of the target. Furthermore, the opportunity to examine the spectrum over a large wavelength range (190 nm-1100 nm) allows for redundant analysis through mathematical corroboration of all wavelengths, providing a high level of reliability of the elucidated values.

WO 01/24699 and its counterpart U.S. Pat. No. 7,280,866 disclose a non-invasive tool for skin disease diagnosis. In-vivo visible- and near-infrared spectra (400-2500 nm) of skin neoplasms (actinic keratoses, basal cell carcinomata, banal common acquired melanocytic nevi, dysplastic melanocytic nevi, actinic lentigines and seborrheic keratoses) were collected by placing a fiber optic probe on the skin. Paired t-tests, repeated measures analysis of variance and linear discriminant analysis were used to determine whether significant spectral differences existed and whether spectra could be classified according to lesion type. Paired t-tests showed significant differences ($p<0.05$) between normal skin and skin lesions in several areas of the visible/near-infrared spectrum. In addition, significant differences were found between the lesion groups by analysis of variance. Linear discriminant analysis classified spectra from benign lesions compared to pre-malignant or malignant lesions with high accuracy.

WO 98/46133 discloses an apparatus for diagnosis of a skin disease site using spectral analysis. The apparatus includes a light source for generating light to illuminate the disease site and a probe unit optically connected to the light source for exposing the disease site to light to generate fluorescence and reflectance light. The probe unit also collects the generated fluorescence and reflectance light and transmits this light to a spectrometer to be analyzed. The spectrometer generates and displays spectral measurements of the fluorescence light and the reflectance light which in together assist the user in diagnosing the disease site. The apparatus makes use of a conventional personal computer using a plug-in spectrometer card to provide a compact and low costs system. The system performs combined fluorescence and reflectance spectral analysis in a quick and efficient manner to provide a powerful tool for dermatologic diagnosis.

SUMMARY OF THE INVENTION

There is need in the art in a novel technique for non-invasive tissue examination, which provides for real-time and relatively fast identification of abnormalities in the tissue condition, e.g. a patient's skin condition. This is because the conventional techniques typically utilize imaging or a point-by-point scan of the entire region of interest, followed by extensive data post-processing.

The present invention provides a novel technique aimed at reducing the amount of data collected and processed for the purpose of identifying and locating a certain abnormality of a tissue portion within the region of interest. Reduction in the data collection/processing enables real time and effective detection of abnormal tissues.

The technique of the present invention relates to screening/inspecting a region of interest for abnormal tissue by utilizing detection of signals (e.g. light responses) from a few locations within a sub-region of the region of interest, analyzing (processing) these signals, determining a direction/path from said sub-region to a successive sub-region along the region of interest corresponding to the highest probability to lead to a location of a maximal degree of abnormality within the region of interest, and generating a corresponding control signal for operating further measurements accordingly. In other words, the invention provides for successively performing a closed loop control and/or a feed forward control to manage a successive scan of (i.e., data collection from) the region of interest based on the previously collected data, thus eliminating a need for scanning and processing respective data from the entire region of interest including parts where a probability of the existence of abnormal tissues is low. To this end, the invention applies an appropriate search algorithm to a limited amount of measured (collected) data. Thus, the invention eliminates a need for scanning the whole region of interest and, more importantly, eliminates a need for time intensive post-processing of extensive data. Instead, data is collected and processed only from a few locations belonging to a set (sub-region) of the region of interest in each cycle (measurement session), generally at least two locations, or preferably at least four spaced-apart locations, rather than collecting data for a whole area of skin (entire region of interest).

Generally, the principles of the present invention can be used in any medical application where a region of interest on a patient's body is to be inspected by scanning to detect and locate one or predetermined abnormalities. It should be understood that the term "scanning" or "scan" signifies sequential inspection of successive sub-regions of the region of interest, and is characterized by a scan direction along which these successive sub-regions are arranged, while such sequential inspection of successive sub-regions does not necessarily utilize any displacement between a measurement probe and the region of interest. The inspection of the sub-region utilizes analysis of measured data collected from a set of at least two spaced-apart locations within said sub-region.

More specifically, the present invention is used for inspection of a patient's skin condition, but it should be understood that the invention is not limited to this specific example. Also, the present invention more specifically deals with optical inspection of a region of interest on a patient's body. However, it should be understood that the invention is not limited to this specific example, and the principles of the invention may be used with any other types of measurements on successive locations on the body by scanning. Such measurements may be active (applying an external field to a region of interest and collecting of a response (signal) of the region of interest to the applied field), or passive (no application of external field). The collected signal (response) may be optical, acoustic, electrical, or a combination of these signals. The measurements may be optical (including pure optical or utilizing ultrasound tagging of light), photoacoustic, or impedance-like. Thus, more specifically, the invention utilizes optical, spectral measurements on a patient's skin and is therefore described below with respect to this specific not limiting example.

A sub-region of interest on a patient's skin, defined by a first set of spaced-apart locations (generally at least two locations) is illuminated, light responses from the illuminated locations are detected, and measured data indicative thereof is generated. The measured data for each location may be in the form of spectral data or a so-called "spectral signature". The measured data (e.g. spectral signature) is then compared to corresponding reference data indicative of a healthy condition of a region of interest (e.g. skin), and a relation between the measured and reference data is determined. In this connection, it should be understood that different conditions of abnormality (e.g. different diseases) might be identifiable by analyzing data pieces corresponding to different types of measurements, e.g. spectral data measured for different spectral regions. Accordingly, a previously compiled database of various types of reference data is used for analyzing the measured data to identify one or more different types of abnormality (should any be present).

Thus, the measured data (e.g. spectral signature) is compared to respective reference data, and a certain parameter (or criterion) describing a relation between these data is determined. This parameter is actually indicative of a deviation of the measured data from the corresponding reference data indicative of healthy condition. Such relation may, for example, be a difference between the measured and reference values/functions, a ratio between them, or any other predetermined functional describing a relation between the measured and reference data (measured data being expressed as a certain function of the reference data).

Typically, measured data corresponds to the presence (or suspected presence) of an abnormal tissue at respective measured location, when the corresponding deviation-related parameter is above or below a predetermined threshold. Such a threshold is determined a priori (based on experimental data). Also provided a priori is a predetermined deviation function, which describes a variation of the deviation-related parameter corresponding to different conditions of a measured location with respect to examined abnormality. Deviation function has a shape characterized by a well-defined global extreme (minimum or maximum). For example, for some skin conditions (such as melanoma), the deviation function may be in the form of a paraboloid. The deviation-related parameter corresponding to the global extreme (typically, minimum) of the deviation function corresponds to the threshold value for the respective abnormality (i.e. maximal deviation of the region of interest with respect to healthy skin), and is thus indicative of a suspected presence (or early detection) of the abnormal condition. A correlation (a difference, a ratio, or any other suitable functional) between the measured value of the deviation-related parameter and that of the global extreme of the deviation function (i.e. the threshold value) indicates a degree of abnormality of the skin condition at the measurement location, and when the deviation-related parameter is equal to (or generally is at a predetermined relation with) the global extreme value of the deviation function, this may for example suggest whether the region of interested should be further examined by biopsy.

Another factor that is preferably initially defined is a set of locations per measurement cycle, e.g. two or four locations. The term "measurement cycle" actually corresponds to a closed loop control session made on a sub-region of the region of interest, and defines measured data (i.e. number of measurements, e.g. corresponding to the number of locations) to be collected for updating the scan direction towards a successive sub-region.

After the parameter is calculated for each location within the set of locations (at least two locations) in the cycle, the value of the deviation-related parameter is mapped for the respective sub-region of the region of interest defined by said set of locations, and a so-called "local minimum" or "local maximum" of the parameter value is determined for said sub-region (by comparing the parameter values to one another). Such a map for the sub-region is used for establishing a preferred (first) scanning direction towards a successive sub-region (set of locations). For the simplest example, let us consider a first sub-region defined by two spaced-apart measurement locations L1 and L2. Respective deviation parameters values DV1 and DV2 are determined as described above, and their relative positions on the deviation function profile are determined. These values DV1 and DV2 are for example such that DV2 is closer to the threshold value TV on the profile of the deviation function, i.e. TV<DV2<DV1. In this case, a first scanning direction is determined towards a second sub-region, defined by at least two locations L3 and L4 both located outside the first sub-region and closer to location L2.

Optionally, the first scanning direction is generated by subtracting the position of the local minimum location from the position of the local maximum location, if a global maximum is sought. Similarly, the first scanning direction is generated by subtracting the position of the local maximum location from the position of the local minimum location, if a global minimum is sought. Alternatively, the first scanning direction is generated by subtracting a central position associated with the set from position of the local maximum location or of the local minimum location, according to which global extreme is sought.

After the first scanning direction is found, a second set of locations (second sub-region) is selected for inspection. The second set of locations is located at a chosen distance from the first set of locations, along the first scanning direction. Measured signals (e.g. light responses) from the locations of the second set are processed as described above, in order to extract a second set of values of said deviation-related parameter and to determine a second scanning direction, as described above. This process is repeated until a location corresponding to the above-described global extreme value of the deviation function is found. The value of said parameter at the global extreme is considered with respect to the pre-defined threshold, in order to make a decision on whether the region of interest includes an abnormality (i.e., suspected area suitable for being sent to biopsy).

The measure signals from different locations in the same sub-region may be collected sequentially or simultaneously. In both cases, processing of the measured signals/data aimed at determination of the relation between the measured and reference data (i.e. determination of the corresponding value of the deviation-related parameter), can be carried separately for each location or simultaneously for all locations.

There is thus provided according to one broad aspect of the invention, a monitoring system for use in managing non-invasive inspection of a region of interest on a patient's body to locate a predetermined abnormality. The monitoring system is connectable to a measurement unit performing said non-invasive inspection and comprises: a memory utility and a processing utility. The memory utility serves for storing reference data comprising: at least one reference response of a body corresponding to a normal condition with respect to at least one abnormality to be detected; and at least one predetermined deviation function corresponding to at least one abnormality to be detected. The processor utility is configured and operable for carrying out the following. The processor utility analyzes first measured data including at least two measured data pieces from at least two first spaced-apart measurement locations respectively within the region of interest and determining for each location a deviation parameter corresponding to deviation of the measured data piece from the reference response corresponding to a normal condition with respect to said predetermined abnormality. The processor utility utilizes the predetermined deviation function to determine, for each of said at least two of the measured data pieces of the first measured data, a relation between the deviation parameter and a predetermined threshold value corresponding to a condition of said predetermined abnormality, and to generate a control signal and communicate it to the measurement unit. The control signal is indicative of a scan direction towards at least one second location to be measured in the region of interest where a degree of said predetermined abnormality is higher than in said at least two first locations. The system thereby enables a closed loop control of a scan direction towards one or more successive locations in the region of interest with higher degree of abnormality based on the analysis of the measured data from at least two preceding locations, and enables the inspection to proceed through locations with increasing degree of abnormality while avoiding measurements at locations in the region of interest where a degree of abnormality is relatively low.

The measurement unit is configured and operable for carrying out non-invasive measurements of one or more properties of a tissue within the region of interest by detecting signals from a plurality of the measurement locations and generating measured data indicative thereof. The measurement unit comprises a control unit configured and operable to be responsive to said control signal from the processing utility and to manage detection of signals from successive locations spaced from previously measured locations along the corresponding scan direction.

In some embodiments of the invention, the measured data piece is indicative of a light signal from a measurement location. The light signal may be a light response of the measurement location to incident light. The light response may comprise one or more of the following: reflected, scattered and excited light.

In some embodiments of the invention, the measurement unit comprises: an optical system configured and operable for carrying out non-invasive optical measurements of one or more properties of a tissue within the region of interest by detecting light signals from a plurality of the measurement locations and generating measured data indicative thereof; and a control unit configured and operable to be responsive to said control signal from the processing utility and to manage the detection of the light signals from successive locations spaced from previously measured locations along the corresponding scan direction.

The optical system may comprise a light source for generating light of multiple wavelengths, and a light detection unit for detecting the light responses and generating for each light response the respective measured data piece in the form of spectral data.

The measured data preferably comprises data indicative of coordinates of the measurement locations corresponding to the measured data pieces.

In some embodiments of the invention, the optical system comprises a fiber bundle connected by its one end to the light source and the light detector and comprising a plurality of illuminating and detecting optical fibers, said optical system being operable for selectively detect light responses originated at different sets of measurement locations, each set being formed by the at least two spaced-apart locations in the region of interest.

At least some of the optical fibers may be operable as both the illuminating and detecting optical fibers, the control unit being configured and operable to selectively shift said at least some of the optical fibers between illumination and detection modes.

The measurement unit may be configured and operable to controllably vary at least one of illumination and detection light patterns to successively detect light from at least one different set of measurement locations.

The reference data preferably comprises a library of a plurality of reference responses corresponding to multiple different types of abnormality.

The system may be configured and operable to process different types of the measured data corresponding to the different types of the detected light responses, thereby enabling identification of more than one type of abnormality in the region of interest.

The at least two first spaced-apart locations are preferably spaced from one another a predetermined distance. Also, the at least one second location is preferably spaced from a first sub-region, defined by said at least two first locations, a predetermined distance.

The processing utility may be configured and operable for creating data indicative of a map of variations of the deviation parameter values in said at least two first measurement locations, and analyzing said map to determine a relation between a profile of the variation of the deviation parameter value and a corresponding profile of the deviation function, and thereby determine said scan direction towards said at least one second location.

According to another broad aspect of the invention, there is provided a monitoring system for use in managing non-invasive inspection of a region of interest on a patient's body to locate a predetermined abnormality, the system comprising: an optical measurement unit configured and operable to inspect said region of interest by scanning successive sub-regions of the region of interest, a memory utility, and a processor utility. The measurement unit comprises an optical system for applying optical measurements to each sub-region by detecting light from at least two spaced-apart locations within said sub-region. The memory utility stores reference data comprising: at least one reference light response of a body corresponding to a normal condition with respect to at least one abnormality to be detected; and at least one predetermined deviation function corresponding to at least one abnormality to be detected. The processor utility is configured and operable for carrying out the following: (i) analyzing first measured data indicative of the detected light responses from the at least two measurement locations of the first sub-region, (ii) determining distribution of a degree of abnormality for said predetermined abnormality in between said at least two measurement locations of the first sub-region, (iii) determining an optimal scan direction from the first sub-region towards a second sub-region where a degree of abnormality is higher than in the first sub-region; (iv) generating a control signal indicative of said optimal scan direction and operating the measurement unit in accordance with said control signal; and (v) repeating steps (i) to (iv) with respect to each successive sub-region, by a closed loop control of the scan direction towards one or more successive sub-regions in the region of interest towards a sub-region with higher degree of abnormality based on the analysis of the measured data from a preceding measured sub-region.

BRIEF DESCRIPTION OF THE DRAWINGS

In order to understand the invention and to see how it may be carried out in practice, embodiments will now be described, by way of non-limiting example only, with reference to the accompanying drawings, in which.

DETAILED DESCRIPTION OF EMBODIMENTS

Figure 1:
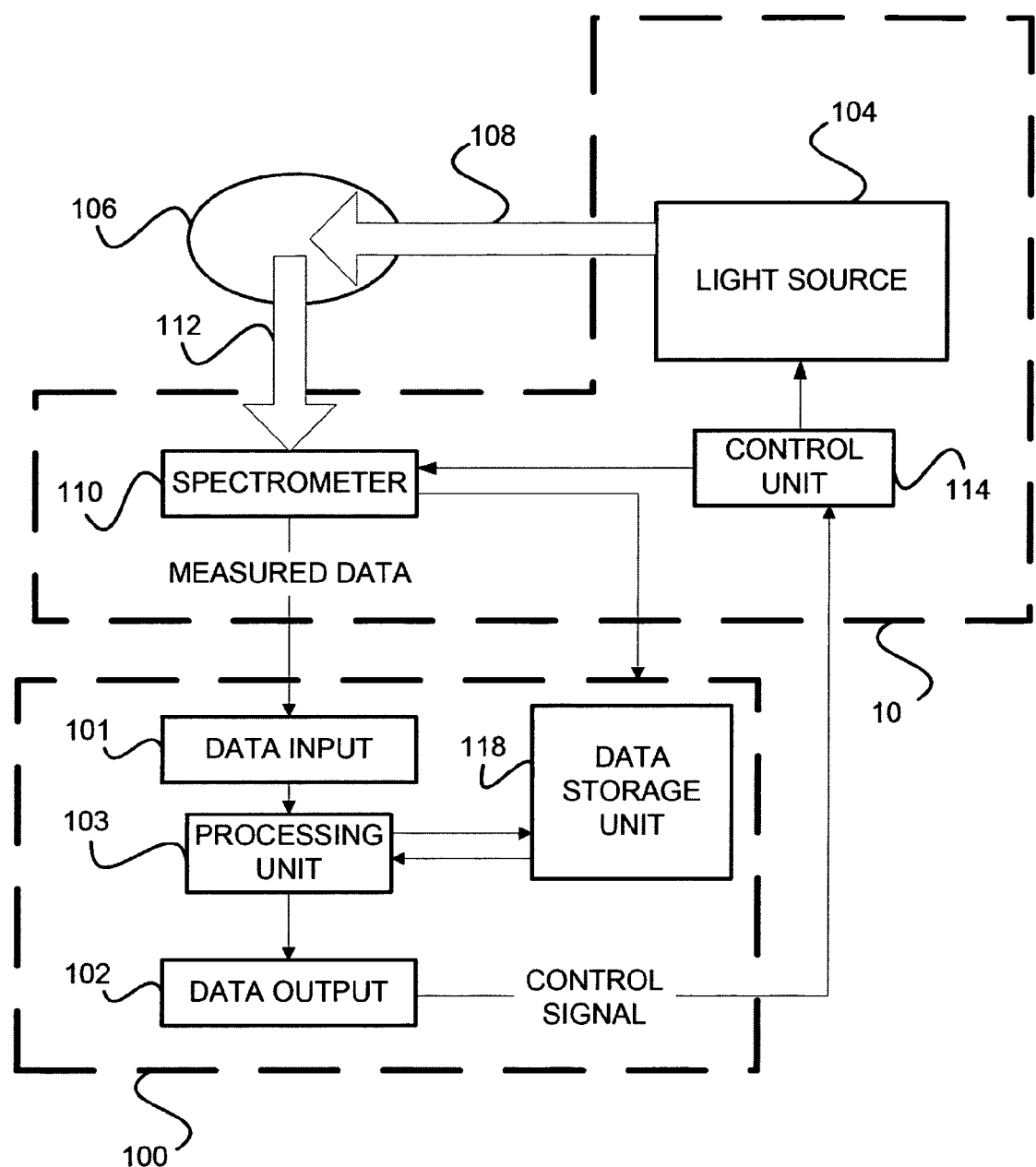
FIG. 1 is a block diagram illustrating a system for monitoring optical inspection of a tissue (e.g. skin lesions) for diseases/abnormalities therein, according to some embodiments of the present invention.

Reference is made to FIG. 1 illustrating, by way of a block diagram, a system 100 of the invention for monitoring a process of optical inspection of a tissue (e.g. skin lesions) for diseases/abnormalities therein. The system 100 is generally a computer system including inter alia data input and output utilities 101 and 102, memory utility 118, and a processing utility 103. The system 100 is associated with a measurement unit 10. The system 100 may be a stand alone system connectable to the measurement unit 10 via wires or wireless signal transmission, or may be integral with the measurement unit 10. The measurement unit 10 is configured and operable for carrying out non-invasive measurements on a region of interest 106 on a patient's body (e.g. skin region). It should be understood that in case the measurement unit 10 and the monitoring system 100 are intended to communicate via wireless signal transmission, either one of them or both might include a respective signal transmitter/receiver capable of appropriately formatting measured data generated by the measurement unit (i.e. in IR, RF or acoustic data format), and possibly also appropriately coding/decoding the measured data.

As indicated above, the present invention may be used with optical spectral measurements on a patient's body (skin) and will therefore described below with respect to this specific but not limiting example. The measurement unit 10 includes an optical system including such main constructional parts as a light source unit 104 and a light detection unit 110 comprising a spectrometer. The optical system might include suitable light directing elements (lens(es), light deflector(s), light guiding element(s), etc.) which are not specifically shown. The light source unit 104 and light detection unit 110 may be accommodated in a common housing or may be implemented as separated units.

Preferably, the optical system comprises a fiber bundle as a light guiding unit including a plurality of illumination and detection fibers. Generally, the same fiber may be selectively operated as an illumination fiber or as a detection fiber, i.e. may be switched between the illumination and detection modes. The use of the fiber bundle arrangement allows for concurrent or sequential detection of light coming from several locations from the illuminated part of the region of interest (probing area) for the same relative position of the fiber bundle with respect to the patient's body.

Also provided in the measurement unit 10 is a control unit 114. The control unit 114 is configured for operating the illumination and detection modes of the optical system. According to the invention, the control unit 114 is operable by a control signal generated by the monitoring system 100 for operating the optical system in an optimal scan direction from the previously inspected sub-region to a successive sub-region of the region of interest. This will be described more specifically further below.

Generally speaking the monitoring system 100 operates as follows. The monitoring system 100 receives and analyses measured data generated by and coming from the measurement unit 10. This measured data was collected during a scan of a first sub-region of the region of interest, (i.e. while collecting measured signals from at least two spaced-apart locations of the first sub-region). The first sub-region may be chosen by a user via a preliminary manual targeting, by setting the measurement unit 100 (its optical system) in a position that enables detection of light responses from the chosen sub-region region of the region of interest. The monitoring system 100 processes the measured data corresponding to the first sub-region, and generates a control signal indicative a first scanning direction for scanning a successive, second sub-region of said region of interest. This first scanning direction is determined as a potential direction towards a location/sub-region of the region of interest having a higher degree of abnormality, i.e. characterized by a deviation parameter value closer to the threshold, based on the results of the first measurement session. Thus, the result of the first measurement session carried out at the first sub-region provides a closed loop control of the operation of the measurement unit with regard to the first scan direction to be taken to locate a second sub-region (set of measurement locations) and apply a second measurement session (cycle) to said second sub-region, and so on.

More specifically, the measurement unit 10 operates to illuminate a part (sub-region) of the region of interest 106 with incident light 108 of one or more spectral ranges generated by the light source 104, and detect by the spectrometer 110 light responses, generally at 112, from a set of locations (at least two locations) within the illuminated sub-region. The light response may be formed by light reflected and/or scattered from the region of interest and/or light excited at the region of interest (luminescence, photoluminescence, fluorescence). The spectrometer 110 generates measured data indicative of the detected light responses. The measured data is transmitted to the monitoring system 100 either directly from the spectrometer 110 (as exemplified in the figure) or via the control unit 114 as the case may be. The measured data may include a corresponding set of spectral signatures for all the locations respectively in said set of locations, and the coordinates of said locations.

The monitoring system 100 receives, via data input utility 101, data indicative of the measured data (spectral signatures) and the corresponding detection locations. The processing utility 103 processes the received data using certain reference data pre-stored in the memory utility 118. The reference data includes a "reference" signal/data (e.g. spectral signature) corresponding to healthy skin or normal condition of the skin with respect to a specific abnormality for which the skin region is inspected. The reference data may include a library of various reference signals (spectral signatures) corresponding to normal conditions with respect to various types of abnormalities which might be found within the region of interest. In this case, the processing utility might operate to select a relevant reference signal to be used for analyzing the received data. Also included in the pre-stored reference data is one or more deviation functions for one or more types of abnormality. The inventors have found that a unique deviation function (profile) can be defined for each type of abnormality (disease) and characterized by a well-defined global extreme (maximum or minimum), for example, being a paraboloid function. The value of the deviation function at such global extreme represents a maximal deviation of the condition of the measurement location with respect to that of a healthy skin. Thus, the deviation function has a global extreme (typically, minimum) corresponding to a predetermined threshold value of a certain deviation parameter (criterion), indicative of the respective abnormality in the measured data.

The processing unit 103 analyzes the received data, determines a relation between the measured and reference data pieces for each measured signal (i.e. for each location), calculates corresponding values of a certain parameter, termed "deviation-related parameter", for all the detection locations respectively. This parameter is indicative of the deviation of the measured signals from the corresponding reference signal. The deviation-related parameter therefore is an expression of the degree of skin abnormality. To this end, the pre-stored deviation function is used to identify a relation (e.g. difference) between these deviation parameter values, for spaced-apart locations in the first measured sub-region of the region of interest, with respect to the predetermined threshold (global minimum of the deviation function). This difference is indicative of a first scan direction from said first sub-region to a further, second sub-region which is supposed to have higher degree of abnormality, i.e. which is supposed to be characterized by deviation parameter value(s) closer to the threshold value.

The pre-stored deviation function is used to identify a difference between these deviation parameter values with respect to the predetermined threshold (global minimum of the deviation function) for spaced-apart locations in the first-scan sub-region of the region of interest. This difference is indicative of a direction in which an optimal scan is to be carried out towards a successive set of locations (sub-region). Based on the so-identified difference, the processing unit 103 generates a control signal to manage a further scan by the measurement unit 10 in an "optimal" scanning direction. The optimal scanning direction points from one set of locations in the region of interest 106 to a successive set of locations in which the degree of abnormality is higher than in the preceding sub-region.

The control unit 114 is in communication with the processing unit 103, and operates the optical system in accordance with the control signal received from the processing unit of the system 100. More specifically, the control unit 103 selects the successive set of locations to be at a chosen distance from the previously scanned set along the scanning direction determined by the processing unit 103. The monitoring system 100 therefore provides a closed loop control of the operation of the measurement unit, to update a scanning direction for each successive cycle based on the data analyses results of the preceding cycle. In each cycle, measurements are performed at a set of locations, the measured data pieces are processed to generate the control signal, and the latter is used to direct the measurement unit 10 to a successive set of locations. This process is performed repeatedly, until a location at which the highest degree of abnormality is identified. The highest degree of abnormality is compared to the predetermined threshold, and this comparison enables a decision to be made on whether the abnormality is suspect and whether a biopsy is necessary. The comparison may be made by medical personnel based on the processing results which might be appropriately output by the system 100 (e.g. displayed).

The closed loop control of the scanning procedure enables to find the highest degree of the skin abnormality in the region of interest by performing optical measurements at a limited number of locations within the region of interest. The limited number of measurements leads to limited data processing, which simplifies the processing procedure and the configuration of the processing unit itself, and allows for a faster inspection procedure, enabling real time tissue examination.

Optionally, the memory utility 118 or another data storage utility is used for storing the results of the inspection procedure (spectral signatures themselves or calculated values of deviation-related parameter, for a plurality of locations in the region of interest). Such stored data may be collected during several inspection procedures to form a "patient history", and used by medical personnel to follow the development of a skin abnormality in time between visits by the patient. The data created during one visit of the patient may be compared to data yielded during one or more previous visits, and changes in the degree of skin abnormality may be calculated in order to help medical personnel diagnose the development of a certain abnormality.

As indicated above, the monitoring system 100 may be separate from and in communication with the measurement unit 10, or may be integral with the measurement unit (e.g. installable into the measurement unit). Optionally, the processing unit 103 is in communication with a user input interface, such as a keyboard, or a keypad, for example, for receiving instructions from a user. The instructions may include commands to start and/or stop a measurement, or to process the measured data (e.g. spectral signatures) in a manner preferred by the user (different data processing techniques are described below, in reference to FIGS. 5a-5c, 6a-6c and 7a-7c). Optionally, the processing unit 103 is associated with an output interface (not shown), such as a display or a speaker, for example, for conveying data to the user. The data conveyed may include, for example, a graphical representation of the measured and/or processed data and/or a sound to warn the user of suspect abnormalities.

In a variant, the distances between the sets of locations are predetermined and optionally equal to each other. In another variant, the distance between a set of locations and a successive set depend of the parameter values at the locations in the set, and is calculated by the processing unit 103. Optionally, the distance depends on the difference between the local minimum and the local maximum within the set. The inventors have found that for a variety of abnormalities, the parameter as a function of location (i.e. deviation function) has a two dimensional bell like shape (profile), and the global extreme is a global minimum. This means that sets of locations within the region of interest at some distance from the global minimum of the deviation function are characterized by a larger difference between the local maximum and the local minimum of the corresponding deviation parameters. Conversely, sets of locations located in the region of interest and close to the global minimum are characterized by a smaller difference between the local maximum and the local minimum of the deviation parameter. Therefore, in some embodiments of the present invention, the distance between a given set and a successive set is an increasing function of the difference between the local maximum and the local minimum of the deviation parameter within the given set of locations.

Figure 2:
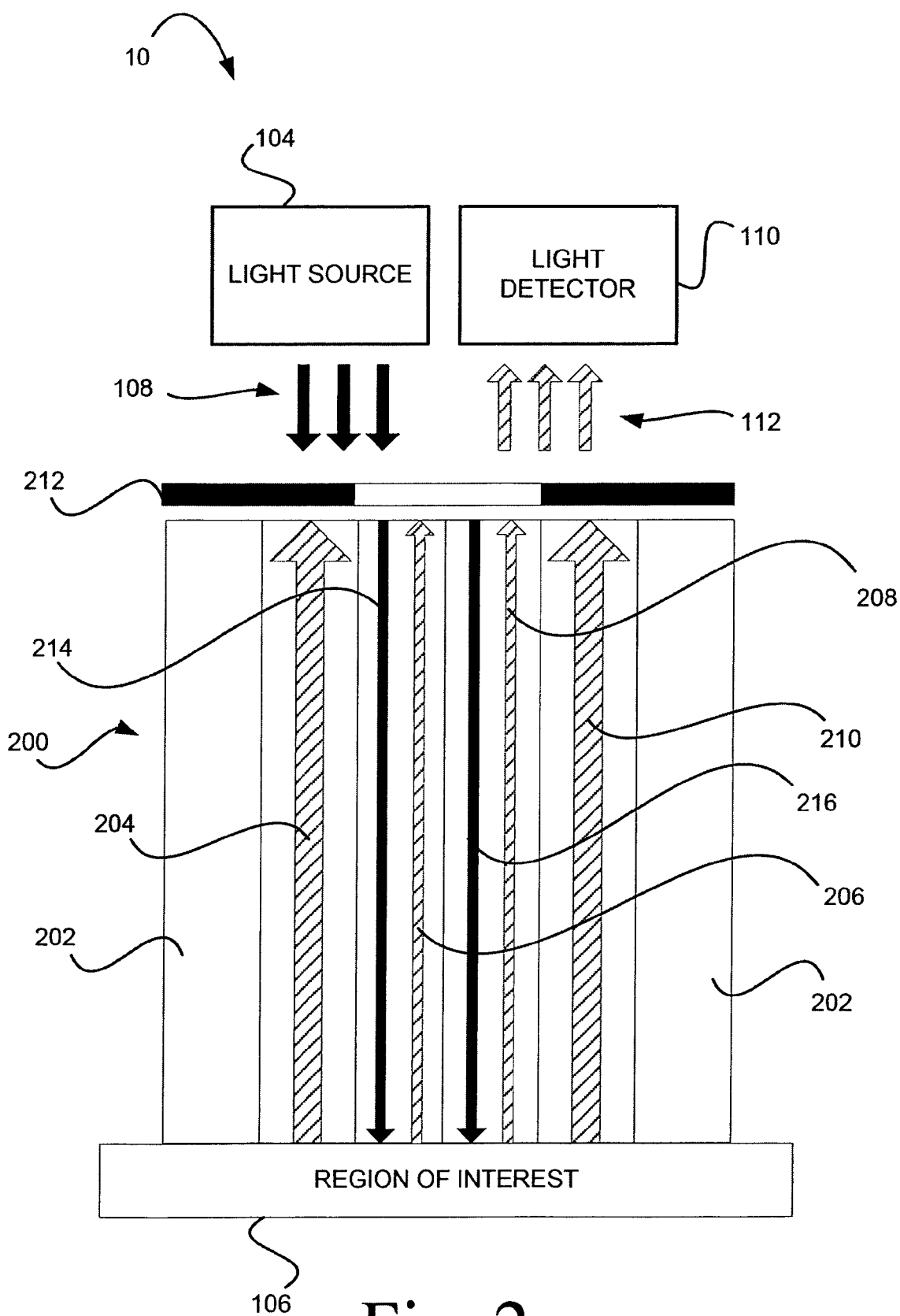
FIG. 2 is a schematic drawing illustrating an optical assembly suitable for use with the system of the invention for illumination and light detection via a bundle of fiber optic wires.

Reference is now made to FIG. 2 which schematically illustrates an example of the configuration and operation of the optical system suitable for use in the measurement unit 10 for implementing the invention. In this example, the optical system includes a light source 104, a light detector (spectrometer) 110, and a fiber bundle 200 of a plurality of optical fibers, generally 202, used to convey illumination light 108 from the light source 104 to a region of interest 106, and for directing collected light 112 returned from the illuminated locations to the detection unit (spectrometer) 110. The collected light 112 includes components of a light response (204, 206, 208, 210) from a corresponding plurality of spaced-apart locations within the illuminated part of the region of interest 106. Each optical fiber is designed for conveying light to and from a respective location of the region of interest. The control unit (114 in FIG. 1) may therefore select locations of the light responses from which are to be detected by the spectrometer for further analysis, by selecting specific fiber(s) and switching them into respective operational modes.

In a variant, the selection of fibers is performed by instructing the spectrometer 110 or the control unit 114 (as the case may be) to ignore light response(s) from one or more fibers corresponding to location(s) outside a desired set of locations, and to analyze only light received via fibers corresponding to locations comprised in the desired set. This may be done by software and/or hardware utilities. For example, the control unit 114 may transmit or allow transmission from the spectrometer 110 to the processing unit 103 the selected light responses 206 and 208, and ignore the light responses 204 and 210.

In another variant, the selection is performed by allowing "desired" light responses to propagate towards the detector while preventing "undesired" to reach the detector, by using a mask 212 placed between the fiber bundle 200 and the spectrometer 110. The mask 212 is operated to selectively prevent light responses from locations outside the desired set (204 and 210) from reaching the spectrometer, and allow passage of light responses from locations comprised in the desired set (206 and 208) to the spectrometer. To this end, the mask may be mechanically shifted to locate a different mask pattern in the optical path of light propagating from the fiber bundler towards the spectrometer (using an appropriate driving mechanism) controlled by the control unit 114, or the mask may be in the form of a spatial light modulator (e.g. liquid crystal based modulator) operated by the control unit to selectively vary the modulating pattern. Similarly, the mask 212 may be used to enable selective illumination of one or more locations in the region of interest. For example, the mask 212 may allow only components 214 and 216 of the illuminating light 108 to reach the region of interest. The same fiber may be sequentially operated as illumination and detection fiber for detection of reflected/scattered light, or may be concurrently operated in both the illumination and detection modes if detection of excited light (e.g. luminescent response) is considered. Reflected, luminescent, and scattered light may react differently to different abnormalities, and one type of light may be more useful than the others to characterize certain types of abnormalities. By limiting the passage of illuminating light by the mask provides for an identification of different types of light response and enables a selection of light response analysis, according to the light response type.

The fiber bundle may be moved to a further set of sub-regions within the region of interest in a predefined scanning direction, upon completing inspection of multiple sub-regions defined by the arrangement and operation of fibers in the fiber bundle in a manner described above (i.e. using the closed loop feed forward control of the scanning direction).

The spectrometer 110 may be a wavelength-tunable analyzer, comprising, for example, one or more chromatic filters in the light path, for selecting light response of one or more desired wavelengths and/or one or more desired ranges of wavelengths for analysis. The light source 104 may also be wave tunable and designed to illuminate the region of interest 116 with light of one or more desired wavelengths and/or one or more desired ranges of wavelengths.

Figure 3:
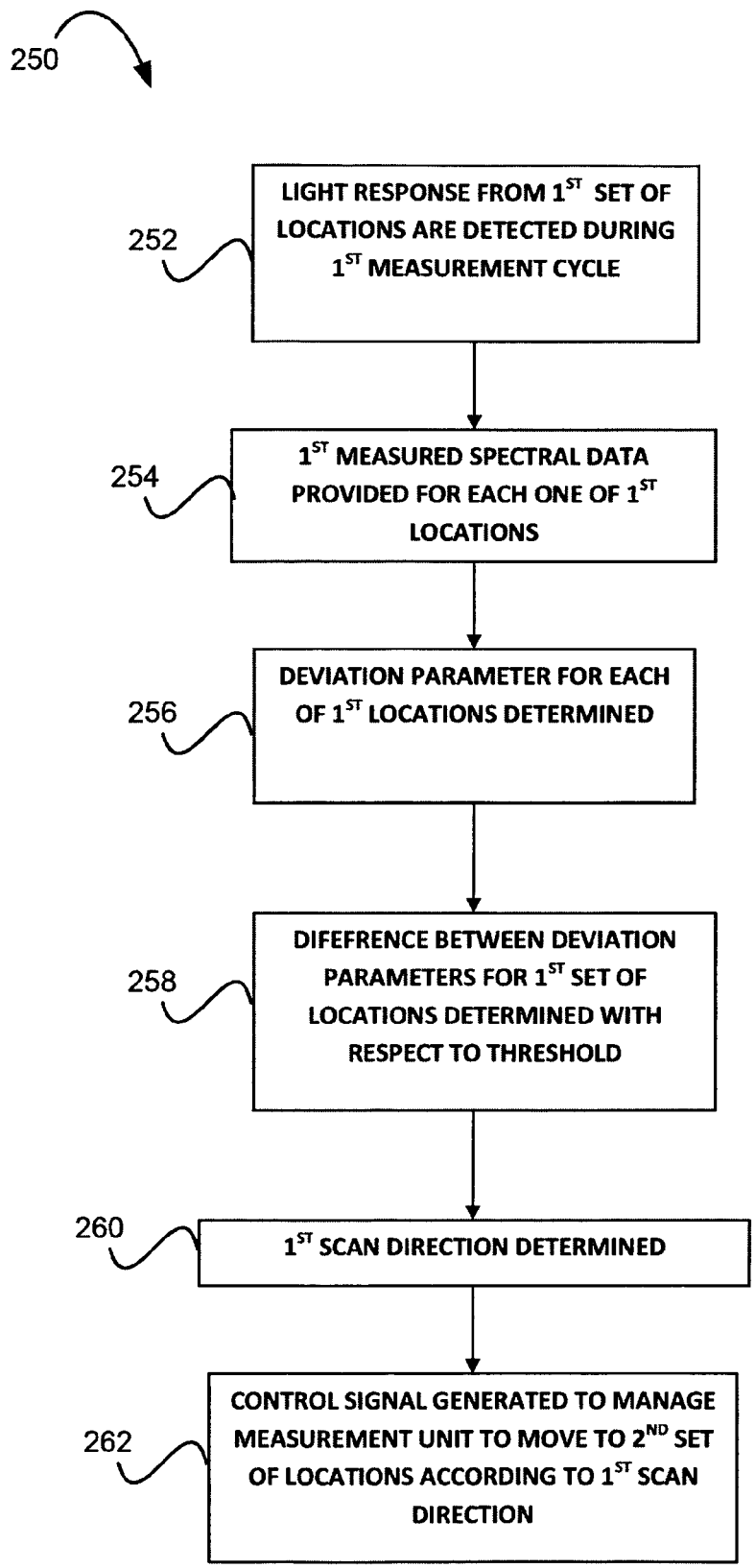
FIG. 3 is a flowchart illustrating an example of a method of the present invention for optical tissue examination.

Referring to FIG. 3, there is shown a flow diagram 250 describing in a self-explanatory manner a method of the present invention for managing the inspection of a region of interest. The measurement unit is operated to detect light response (step 252) from a plurality of spaced-apart locations (at least two or preferably at least four locations) in a first set of locations (i.e. in a first sub-region of the region of interest), and to provide measured (e.g. spectral) data for each of these locations (step 254). As indicated above, the first sub-region is generally chosen by a user via a preliminary manual targeting. The processor unit operates to analyze the measured data to determine a deviation parameter value for each of these locations (step 256) using corresponding reference data, and to determine a difference between the deviation parameter values with respect to the corresponding threshold (step 258) using the corresponding deviation function. Based on this difference, the processing unit operates to determine an optimal direction for the first scan (step 260) towards a second set of spaced-apart locations, and to generate a control signal (step 262) indicative of an optimal scan towards the second sub-region to manage the measurement unit to move toward the second set of locations.

Figure 4A:
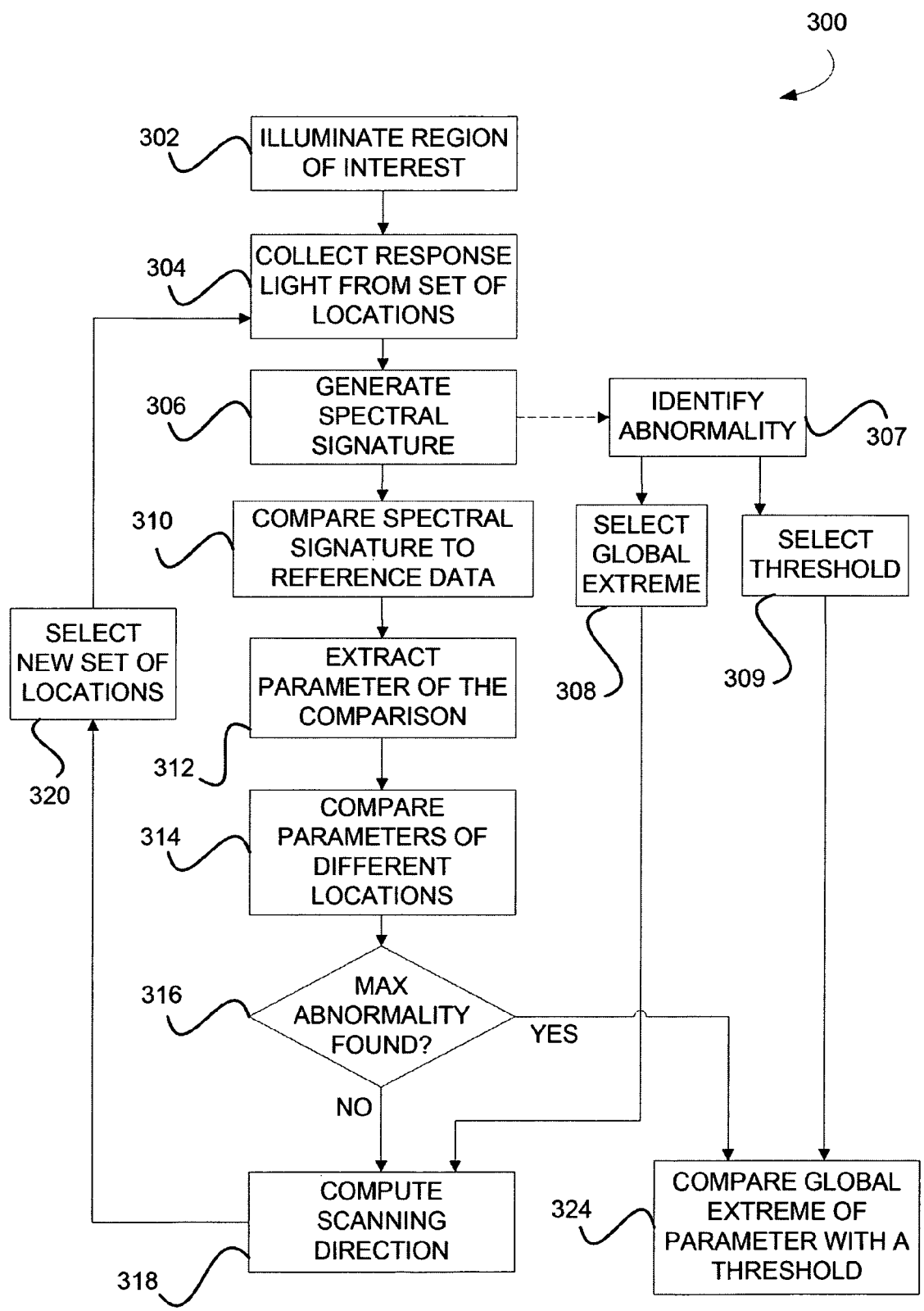
FIGS. 4a-4b are flowcharts exemplifying of data processing method (an algorithm) suitable for use in the invention for detecting an updated scan direction (by locating a global extreme of a chosen parameter on a patient's skin)

FIG. 4a shows a flowchart according to a more specific but not limiting example of a method of the present invention for optical tissue examination. At least a sub-region of the region of interest is illuminated as described above (step 302), and light responses from a limited set of illuminated locations are detected (step 304). The detected light response may include reflected light, and/or scattered light, and/or fluorescent light. These types of light may be identified and analyzed separately, as described above. At 306, spectral data (spectral signature) corresponding to each light response coming from each location is provided (output of the spectrometer). At 307, the abnormality is identified. This may be done by a comparison of the measured spectral signature to a database containing spectral signatures indicative of a plurality of skin diseases. The knowledge identity of the abnormality enables a choice of global extreme to be sought (308), and a determination of the threshold (309), as explained above. The identification of the abnormality may be performed by a processing unit, or may be performed by a user, such as a doctor, according to other techniques known in the art. The subsequent choice of global extreme and the determination of the threshold may be received by the processing unit from an outside source, for example from a user via a user interface.

The spectral signatures generated at 306 are processed, in order to generate a direction of scan. The direction of scan points from one set of locations of the region of interest to a successive set of locations in which the probability of higher degree of skin abnormality is higher. More specifically, the processing includes comparing the spectral signatures to reference data indicative of healthy skin (310), extracting a deviation-related parameter of the comparison (312) for each location, and comparing said parameters of the different locations (314). At 316, a check is made to establish whether the maximal degree of abnormality in the region of interest has been found, according to the values of parameters in the set. If the comparison of the different locations does not yield the global extreme, a scanning direction is computed (318) according to the comparison of 314 and according to the choice 308 of the sought out global extreme, and a new set of locations is selected (320) at the chosen distance from the previous set, and along the direction of scan determined in the processing of spectral signatures of the previous set. The selection of the new set is implemented by appropriately operating the optical system of the measurement unit, as described above. Steps 304-318 are repeated for the new set, until the global extreme of the parameter has been identified. As mentioned above, the deviation-related parameter is so defined that a global extreme (maximum or minimum) thereof in the region of interest indicates the maximal degree of abnormality (maximal deviation from data indicative of healthy skin) in the region of interest. Optionally, computing the scanning direction includes computing the distance between the given set of locations and the next set of locations, as mentioned above.

At 324, when the global extreme is found, a value of the global extreme is compared to a predetermined threshold selected at 309, in order to assess the gravity of the abnormality, and optionally to decide whether the maximal degree of abnormality has reached a level that makes a biopsy of the region of interest necessary or recommendable.

Figure 4B:
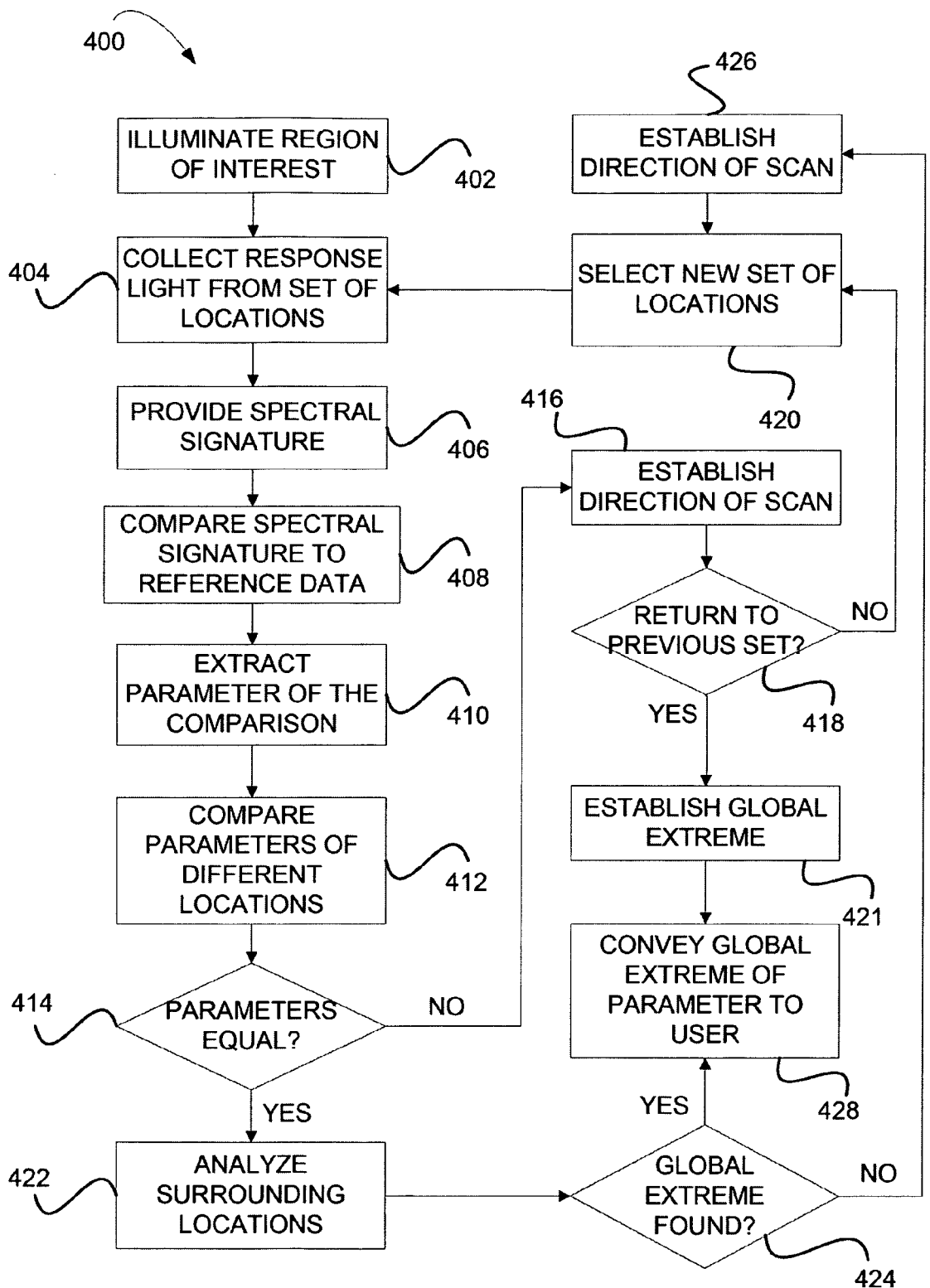

FIG. 4b is a flowchart illustrating an example of a data processing method (an algorithm) suitable for use in the invention for detecting an updated/optimal scan direction (by locating a global extreme of a chosen parameter on a patient's skin);

The steps 402 to 412 are analogous to the steps 302-306 and 310-314 shown in FIG. 4a and described above. At 414, a check is performed to determine whether the parameters corresponding to locations belonging to a given set are equal or close to each other, for example, within a predetermined divergence from an average of the parameters. The divergence may depend on the characteristics of the optical system. If these parameters are not found to be equal or close, a direction of scan is established at 416, as explained above. Optionally, as mentioned above, a distance of scan is also calculated.

At 418 a check is made to determine whether a successive set of locations is located at the distance of scan along the direction of scan in a set of locations previously analyzed. If the new set of locations has not been previously analyzed, the new set of location is selected (420), and steps 404 and the subsequent steps thereof are repeated for the new set of locations. If the new set is a previously analyzed set, it is highly probable that location of the global extreme is within the given set and the set previously analyzed. At 421, the values of the parameters corresponding to locations of the given and previously analyzed sets are compared, and the extreme thereof is identified as the global extreme. At 428, the global extreme is conveyed to a user. Optionally, the global extreme is compared to a threshold, as described above in step 324 of FIG. 4a. Optionally, the type of abnormality is identified, as described above in step 326 of FIG. 4a.

If at 414 the parameters within the set are found to be equal or close to one another, at 422, there is a probability that the global extreme is found at a location within the given set. To ensure that this is so, the locations or sets of locations surrounding the given set are analyzed (step 422), according to steps 404-412. The results of this analysis are assessed (step 424). If the analysis and processing of data from such surrounding locations or surrounding sets of locations yield parameters that are farther from the sought out global extreme or are about equal to the parameters found in the given set, the local extreme in the given set is identified as the global extreme in the region of interest. The global extreme is therefore conveyed to the user (step 428). If one or more of the surrounding locations corresponds to a parameter that is closer to the global extreme and not about equal to the parameters of the given set, the global extreme is not in the given set. At 426, a direction of scan is therefore established from the given set to the location or set in which the parameter approaches the chosen global extreme. At 420, a new set of locations is selected according to the direction and distance of scan. The step 404 and the subsequent steps are repeated for the new set of locations.

Figure 5A:
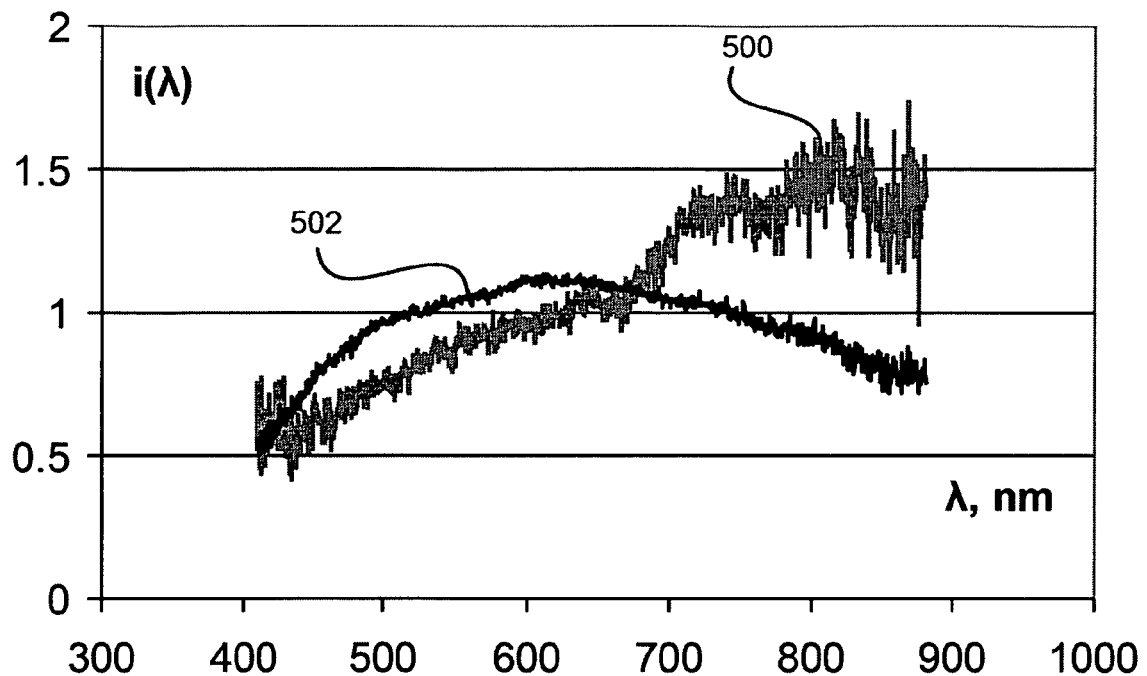
FIGS. 5a-5c are experimental results graphically illustrating spectral signature corresponding to the measured light response of a region of interest on a patient's skin and analysis of this data vs reference data for detection of melanoma.
Figure 5B:
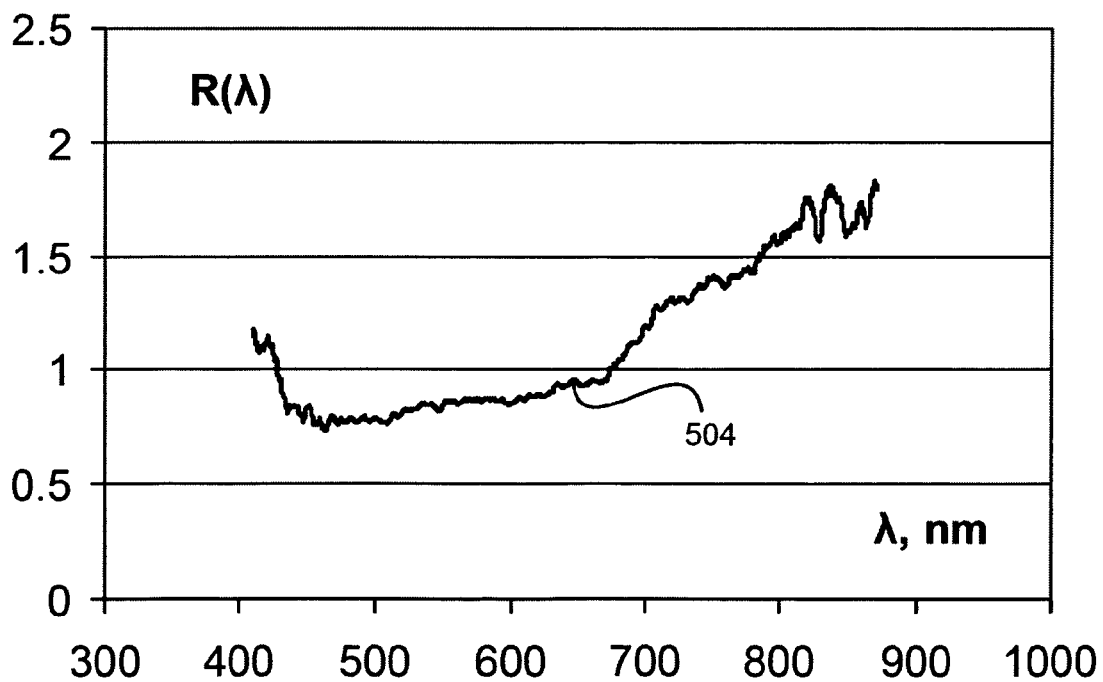
Figure 5C:
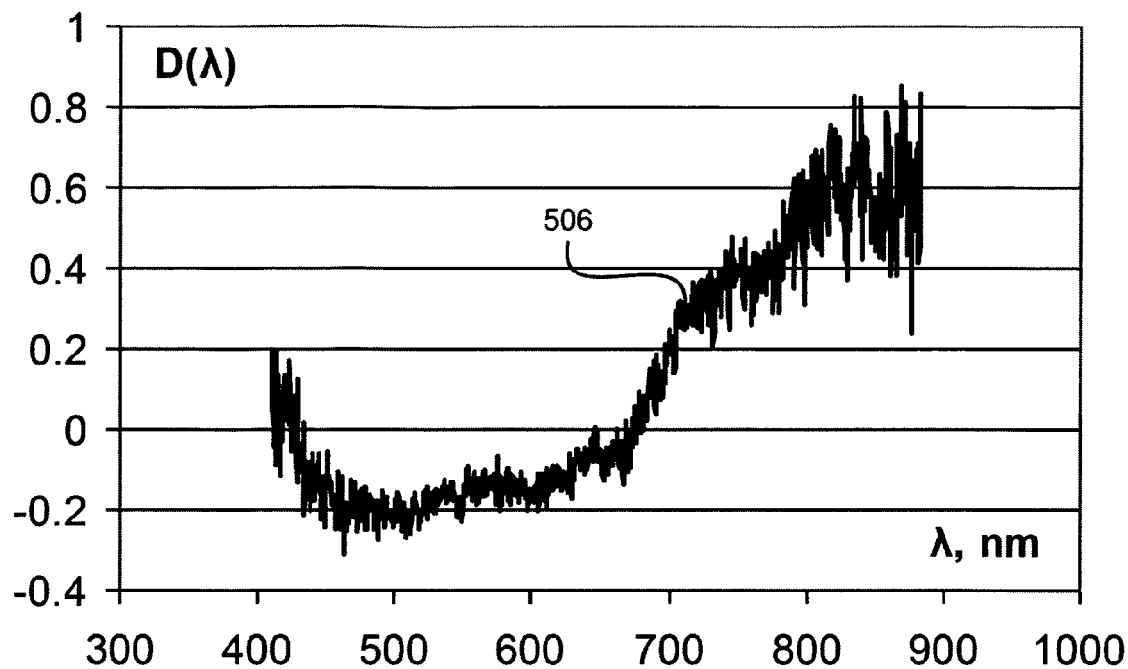

Reference is now made to FIGS. 5a-5c showing experimental results of the present invention for detection of melanoma. FIGS. 5a-5c graphically illustrate measured data (spectral signature) corresponding to the measured light response from a certain location in a region of interest on a patient's skin and analysis of this data vs corresponding reference data. In FIG. 5a, a spectral signature 500 from a location on a patient's skin affected by melanoma is compared to reference spectral data 502 indicative of healthy skin. In FIG. 5b, a first example of a suitable relation function 504 for said location is shown. The relation function R(λ) for a specific location is defined as the quotient $$R(\lambda) = \frac{i_n(\lambda)}{i_h(\lambda)} \quad \text{(equation 1)}$$

where $i_n(\lambda)$ is a normalization of light response intensity corresponding to affected skin, and $i_h(\lambda)$ is a normalization of light response intensity corresponding to healthy skin, and are determined as follows:

$$i_n(\lambda) = I_n(\lambda)/I_n^{(tot)}; I_n^{(tot)} = \int I_n(\lambda)d\lambda \quad \text{(equation 2)}$$

$$i_h(\lambda) = I_h(\lambda)/I_h^{(tot)}; I_h^{(tot)} = \int I_h(\lambda)d\lambda \quad \text{(equation 3)}$$

where $I_n(\lambda)$ is the measured intensity of light response coming from the specific location of affected skin, while $I_h(\lambda)$ is the measured intensity of light response coming from healthy skin.

Because measured intensity changes with position, the normalization is useful for eliminating intensity dependence of the measurement and enabling comparison between measurements taken at different locations. The relation function R(λ) for a location identified by coordinates (x,y) is denoted by $R_{xy}(\lambda)$.

A suitable example of a deviation parameter extracted from/corresponding to the relation function $R_{xy}(\lambda)$ for characterizing deviation of lesion skin spectra from healthy skin spectra at a location (x,y) is a mean derivative $K_{xy}$ of a spectrum in a specified range of wavelengths, where $$K = \frac{\int_{\lambda_1}^{\lambda_2} \frac{dR}{d\lambda} d\lambda}{\lambda_2 - \lambda_1} \quad \text{(equation 4)}$$

A global maximum of the parameter K in the region of interest is indicative to the highest degree of abnormality (i.e. deviation from healthy skin spectra) in the region of interest. If global minimum is considered, (−K) parameter is used.

In FIG. 5c, a second example of a relation function 506 is shown. The relation function D(λ) for a specific location is defined as the difference $$D(\lambda) = i_n(\lambda) - i_h(\lambda) \quad \text{(equation 5)}$$

The relation function D(λ) (506) for a location identified by coordinates (x,y) is denoted by $D_{xy}(\lambda)$.

A suitable example of a deviation parameter extracted from the relation function $D_{xy}(\lambda)$ for characterizing deviation of lesion skin spectra from healthy skin spectra at a location (x,y) is a root mean square $P_{xy}$ in a specified range of wave lengths, where $$P = \sqrt{\frac{\int_{\lambda_1}^{\lambda_2} D^2(\lambda)d\lambda}{\lambda_2 - \lambda_1}} \quad \text{(equation 6)}$$

A global maximum of the parameter P in the region of interest is indicative to the highest degree of abnormality (i.e. deviation from healthy skin spectra) in the region of interest.

Figure 6A:
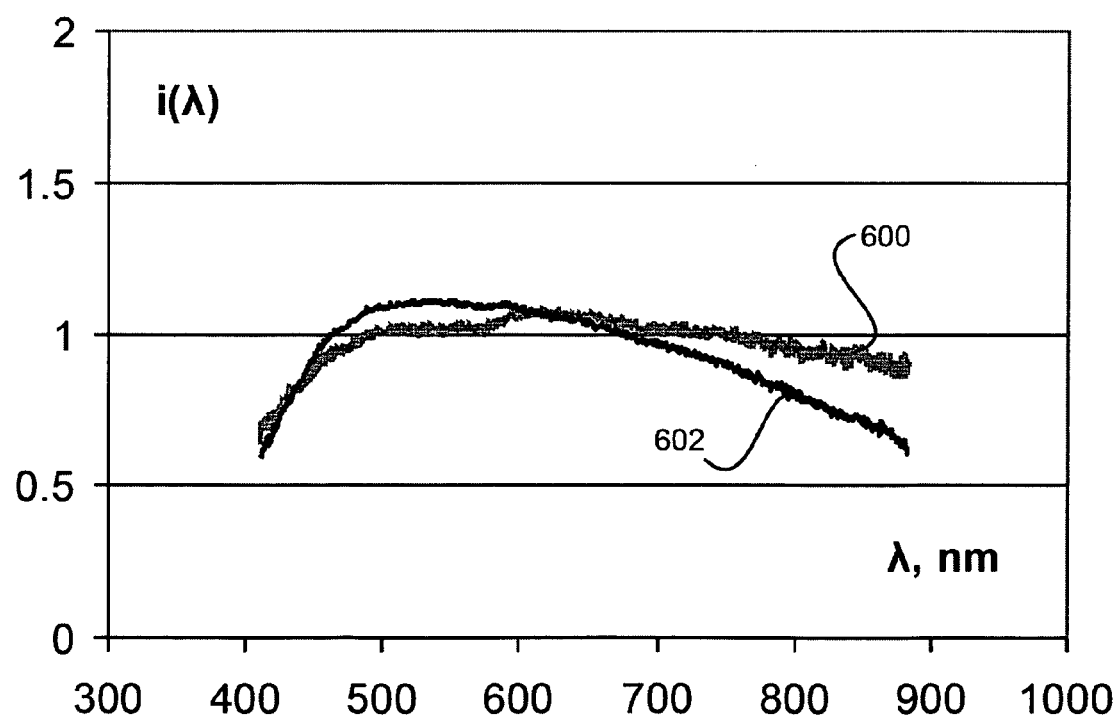
FIGS. 6a-6c are experimental results graphically illustrating spectral signature corresponding to the measured light response of a region of interest on a patient's skin and analysis of this data vs reference data for detection of seborrheic keratosis.
Figure 6B:
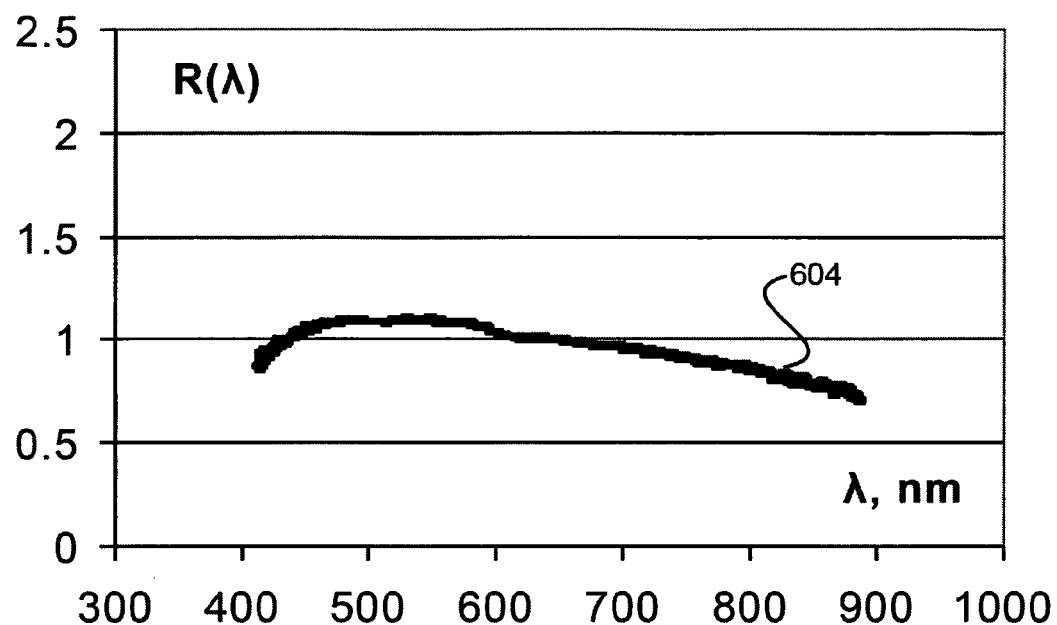
Figure 6C:
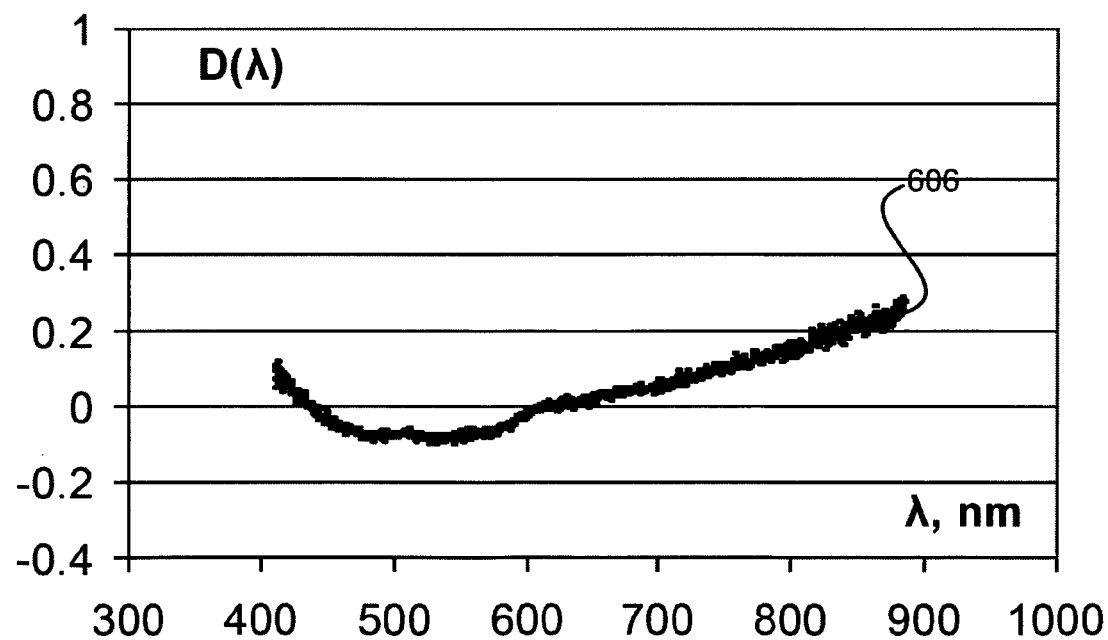

FIGS. 6a-6c are experimental results graphically illustrating a spectral signature corresponding to the measured light response of a location in a region of interest on a patient's skin and analysis of this data vs reference data for detection of seborrheic keratosis. Affected skin spectral signature 600 is compared to healthy skin spectral data 602. A quotient relation function $R_{xy}(\lambda)$ (604) may be calculated for a location denoted by coordinates (x,y). A mean derivative $K_{xy}$ is calculated, to indicate a degree of abnormality of the affected skin. Similarly, a difference relation function $D_{xy}(\lambda)$ (606) may calculated for a location denoted by coordinates (x,y), and a root mean square $P_{xy}$ may be extracted to indicate a degree of abnormality of the affected skin.

Figure 7A:
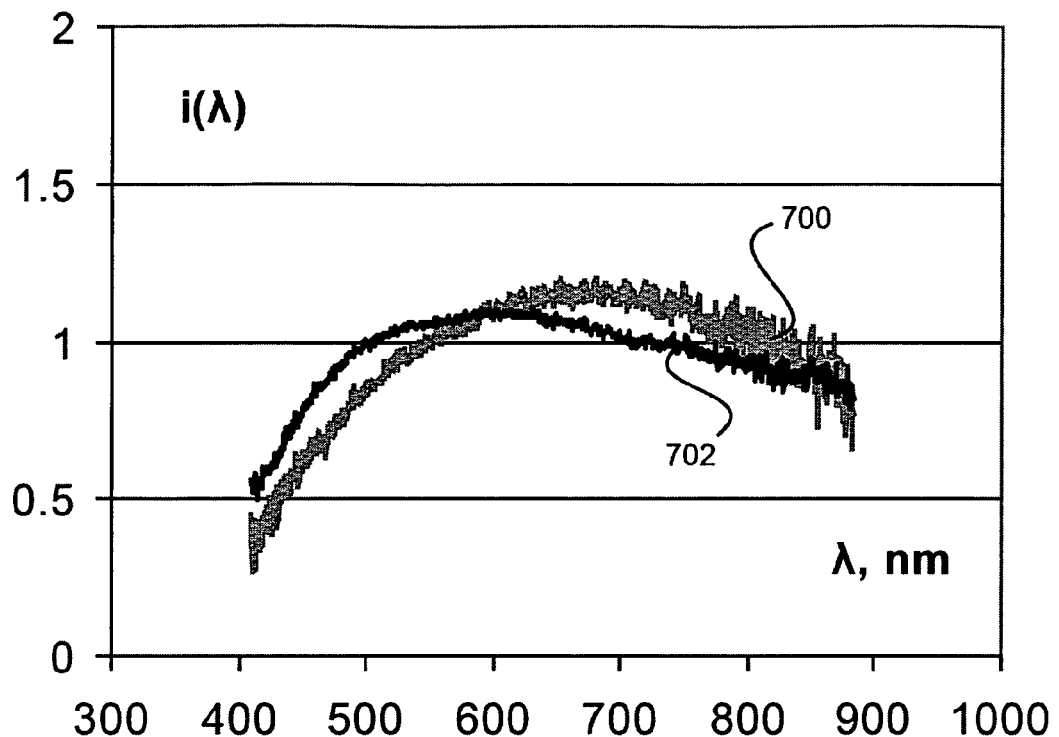
FIGS. 7a-7c are experimental results graphically illustrating spectral signature corresponding to the measured light response of a region of interest on a patient's skin and analysis of this data vs reference data for detection of Dysplastic Nevus.
Figure 7B:
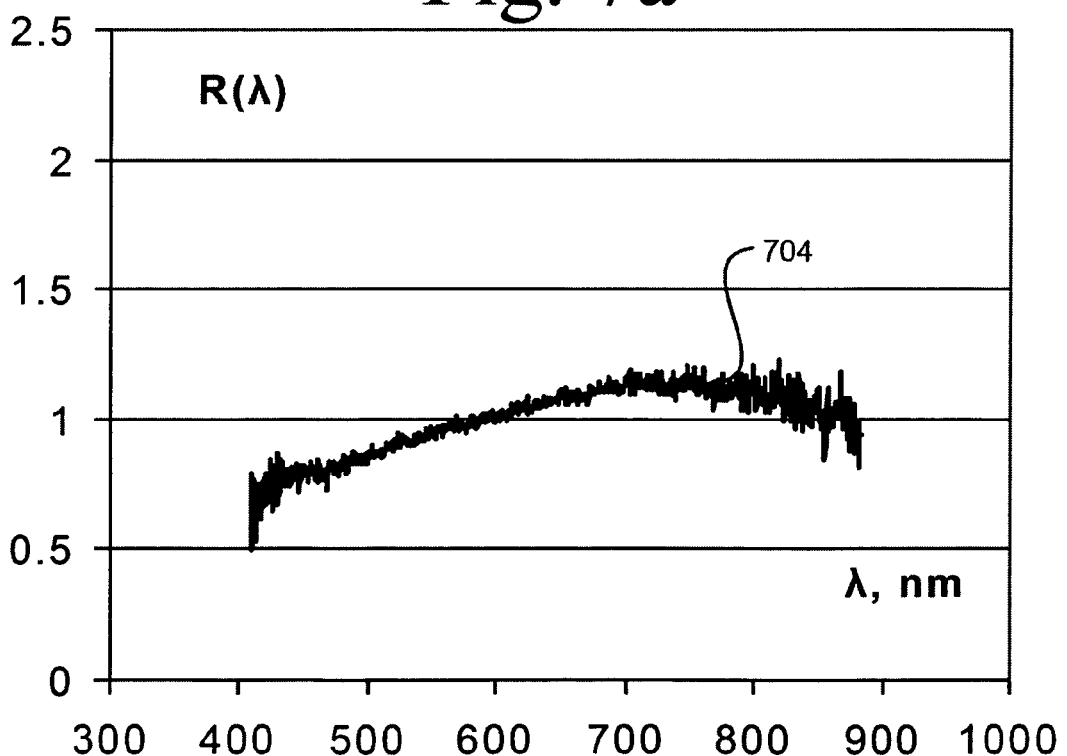
Figure 7C:
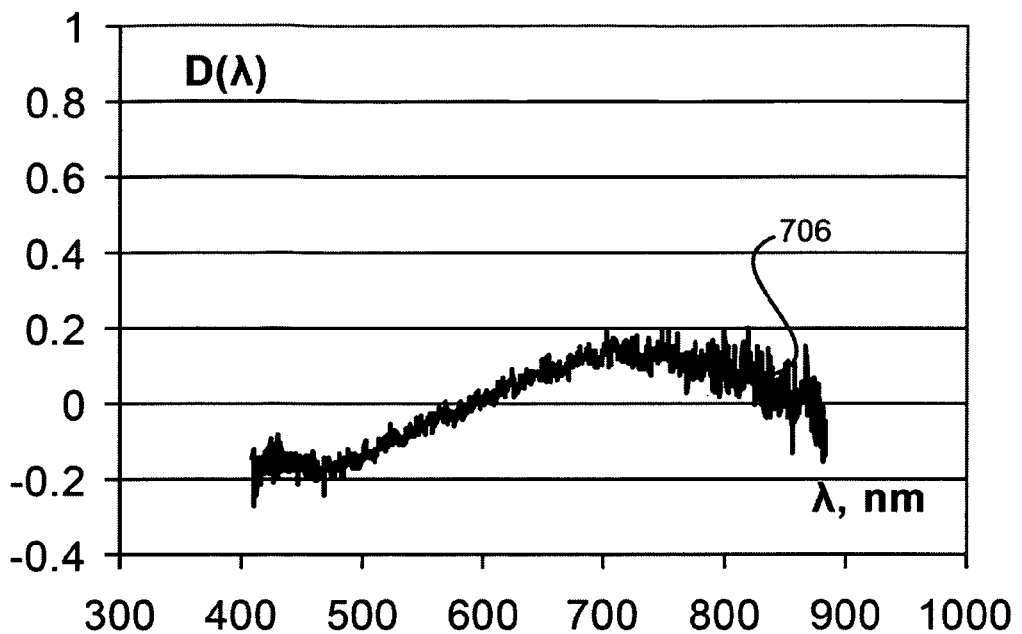

FIGS. 7a-7c are experimental results graphically illustrating a spectral signature corresponding to the measured light response of a region of interest on a patient's skin and analysis of this data vs reference data for detection of dysplastic nevus.

Affected skin spectral signature 700 is compared to healthy skin spectral data 702. A quotient relation function $R_{xy}(\lambda)$ (704) may be calculated for a location denoted by coordinates (x,y). A mean derivative $K_{xy}$ is calculated, to indicate a degree of abnormality of the affected skin. Similarly, a difference relation function $D_{xy}(\lambda)$ (706) may calculated for a location denoted by coordinates (x,y), and a root mean square $P_{xy}$ may be extracted to indicate a degree of abnormality of the affected skin.

FIGS. 7a-7c show that different types of abnormalities that may be identified by determining a relation function (for example R and/or D), and extracting a suitable deviation parameter from the relation function. Furthermore, each type of abnormality is characterized by a unique spectral signature.

Figure 8A:
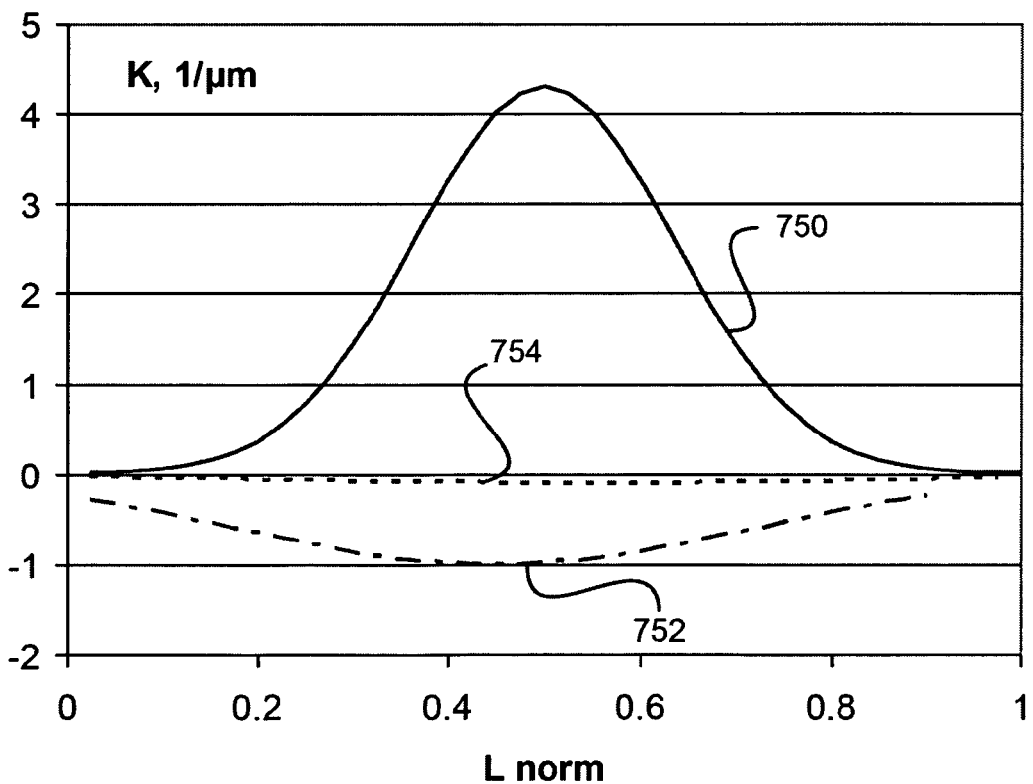
FIGS. 8a-8b exemplify deviation functions (i.e. variation of deviation-related parameter along measurement locations), for different types of abnormalities.
Figure 8B:
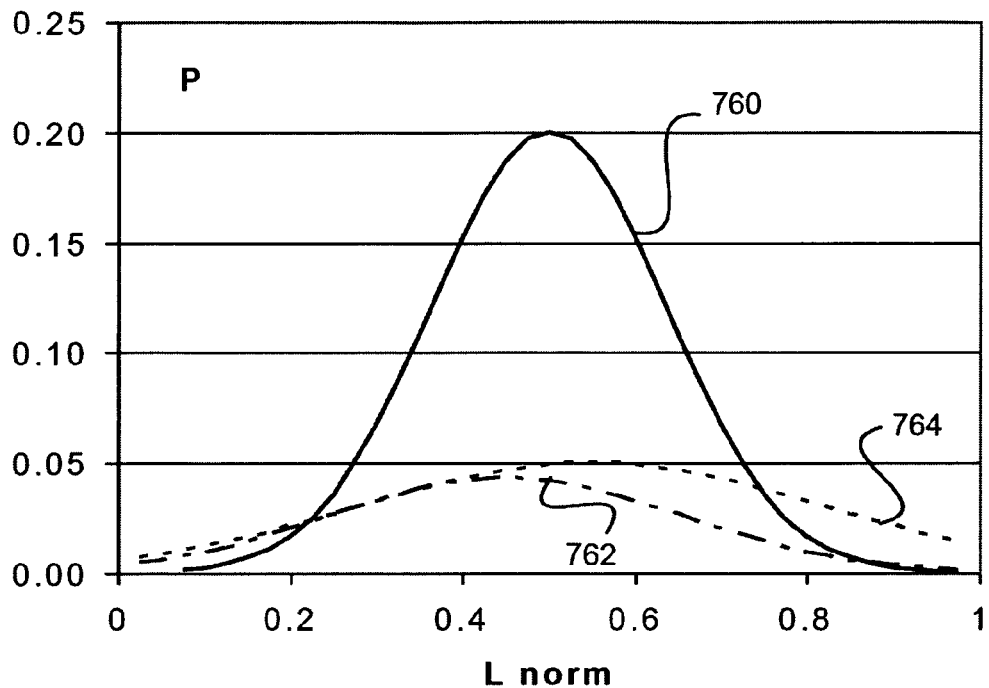

FIGS. 8a and 8b exemplify different types of deviation function (deviation-related parameter as function of position along the inspected region) for different types of abnormality. In the example of FIG. 8a, the deviation-related parameter is represented by mean derivative (K) of the relation function (describing a relation between the measured and reference spectral data). In the example of FIG. 8b, the deviation-related parameter is represented by root mean square (P) of the relation function. Thus, FIG. 8a shows three graphs 750, 752 and 754 corresponding to mean derivative (K) as a function of position normalized by a size of lesion, for respectively, melanoma, seborrheic keratosis, and dysplastic nevus. It is noted that for melanoma, a well-defined global maximum of K is found having a value of 4.3 $\mu m^{-1}$, for seborrheic keratosis a well-defined global minimum of K is found having a value of −1 $\mu m^{-1}$, and for dysplastic nevus a well-defined global minimum of K is found having a value of 0.12 $\mu m^{-1}$. FIG. 8b shows three graphs for root mean squares (P) as a function of normalized position, for melanoma (graph 760), seborrheic keratosis (graph 762), and dysplastic nevus (graph 764). The root mean square functions have been experimentally obtained for a suspected presence (or early detection) of the above skin conditions. It is noted that for melanoma, a well-defined global maximum of P is found having a value of 0.20, for seborrheic keratosis a well-defined global maximum of P is found having a value of 0.048, and for dysplastic nevus a well-defined global maximum of P is found having a value of 0.032. As mentioned above and as seen in the present graphs, the shapes/profiles of the P and K variations along the measurement locations for the above skin diseases are bell-shaped and characterized by well-defined global extremes.

Figure 9:
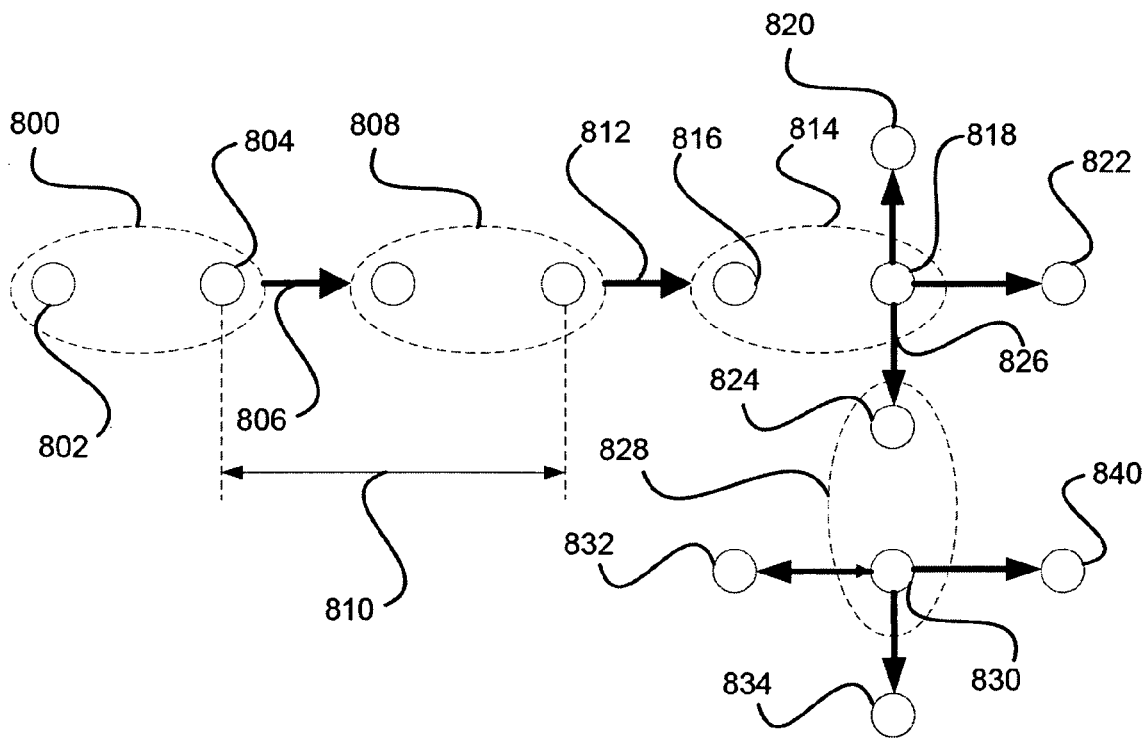
FIG. 9 is a schematic illustration of an example of the technique of the present invention for searching for a global extreme value of the deviation-related parameter, where the search is performed by successive analysis and processing of spectral light response from sets including two locations.

FIG. 9 is a schematic illustration of an example of the technique suitable to be used in the present invention for searching for a global extreme value of the deviation-related parameter, where the search is performed by successive analysis and processing of spectral light responses from sets of locations each including two locations. FIG. 9 illustrates how method 300 of FIG. 4a and data processing algorithm 400 of FIG. 4b are applied in the search of a global extreme.

Initially, a set of locations 800 is selected, including two locations 802 and 804. The distance between locations 802 and 804 may be 3-6 times larger than a cross-sectional dimension (diameter) of an optical fiber (which is about 0.2-1 mm). Light responses of these locations to incident light are detected, either simultaneously or sequentially. Spectral signatures are generated from the collected light responses, and deviation parameter values are calculated for locations 802 and 804. The parameters are compared, and a local maximum and local minimum are determined within the set 800. If the global extreme sought is a global maximum, a direction of scan 806 is determined pointing from the local minimum location to the local maximum location. If the global extreme sought is a global minimum, a direction of scan 806 is determined pointing from the local maximum location to the local minimum location.

For example's sake, the sought out extreme is a global minimum. Again for example's sake, the location 802 is characterized by the local maximum, while the location 804 is characterized by the local minimum. The direction of scan 806 therefore points from the location 802 to the location 804. A second set 808 is therefore selected being spaced a distance 810 away from the first set 800 in the direction 806. The distance 810 may be a preset one (for example about 1 mm). The distance between the preceding and successive sub-regions (sets of locations) may depend on the deviation parameter values, or more specifically on the difference between the values in the preceding set.

The second set 808 is analyzed and the spectral signatures are processed to generate a second direction of scan 812, and optionally a second distance of scan. The third set 814 is analyzed and it is found that the locations 816 and 818 are characterized by equal or almost equal parameters. For example, the parameters at 816 and 818 may be within a predetermined deviation from an average of the parameters. At this point, locations surrounding the location closest to the edge of the current path (i.e. location 818) are analyzed. The location 818 has been picked randomly, and the locations 820, 822, and 824 are analyzed. In a variant, more than three surrounding locations are analyzed.

The deviation parameter at the location 822 is found to be greater than or about equal to the parameter at location 818. This establishes the location 818 as that characterized by a minimal parameter along the line defined by connecting the locations in set 800, 808, and 814. The analysis/processing is therefore to be performed along a line intersecting (preferably parallel) to the above defined line. The parameter at the location 820 is found to be greater than the parameter at 818, and the parameter at 824 is found to be smaller than the parameter at 818.

Since the extreme sought is a global minimum, the new direction of scan 826 points from 818 to 824. The fourth set analyzed is set 828 including location 824 and 830. In a first example, the parameter at 824 is found to be smaller than the parameter at 830. The direction of scan generated by an analysis of the set 828 would therefore point to a previously examined set (i.e., set 814). Therefore the parameter at 824 is the local minimum along the line defined by direction of scan 826. Since the inventors have found that the graphical representation of some parameters against measured locations has a paraboloid or bell like shape, then once the local minimum along a first line has been found, the local minimum along a line to the first line and intersecting the first line at said local minimum of the first line is the global minimum.

In a second example, the parameters at location 824 and 830 are found to be equal or almost equal to each other. The locations 832, 834, and 840 surrounding the location 830 are examined. The parameters at 832, 834, and 840 are found to be greater than or about equal to the parameter. Therefore the parameter at location 830 corresponds to the global minimum.

Figure 10:
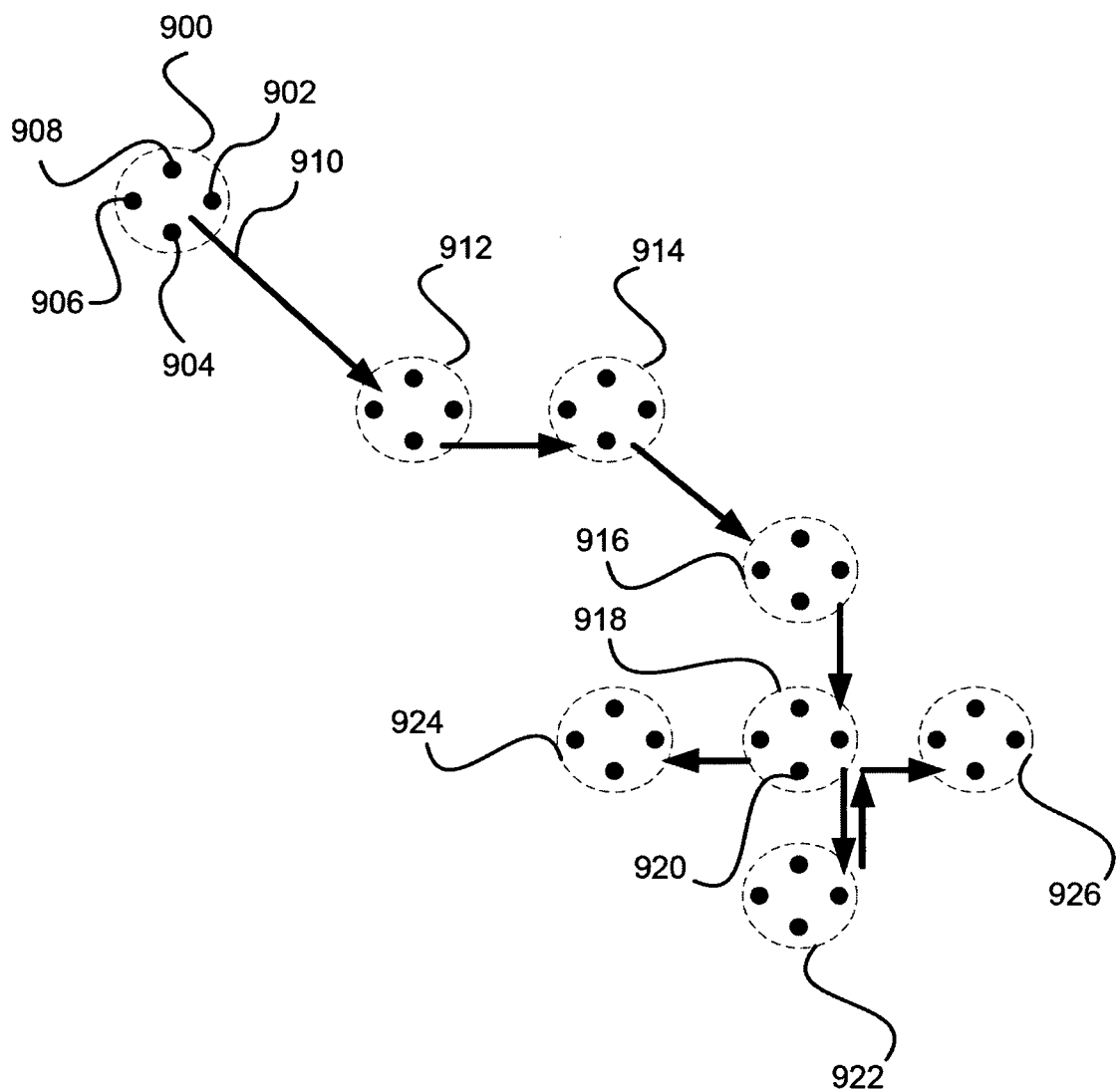
FIG. 10 is a schematic illustration of an example of the technique of the present invention for searching for a global extreme value of the deviation-related parameter, where the search is performed by successive analysis and processing of spectral light response from sets including four locations in a cross pattern.

FIG. 10 is a schematic illustration of an example of the technique of the present invention for searching for a global extreme value of the deviation-related parameter, where the search is performed by successive analysis and processing of spectral light responses from sets including four locations in a cross pattern.

The search for a global minimum starts in the set 900, which includes locations 902, 904, 906, and 908. After a spectral analysis and data processing for each location of the set 900, the local minimum of the parameter is found to correspond to the location 902 and the local maximum of the parameter is found to correspond to the location 908. The direction of scan 910 is determined by connecting the location 908 to location 902. The successive sets are sets 912, 914, 916, and 918. At 918, the location 920 is found to correspond to the local minimum along the path, and the set 922 is examined. However, the direction/path determined by the examination (spectral analysis and data processing) of set 922 points back to the set 920. Furthermore, it is found that the parameter at 920 is smaller than the parameters found at any location within the set 922. To be on the safe side, surrounding sets 924 and 926 are examined, and it is found that all the parameters thereof are either greater than or about equal to the parameter at 920. The parameter at 920 is therefore identified as the global minimum.

Thus, the present invention provides a simple technique enabling to facilitate search for and detection of an abnormality in a region of interest on a patient's body. The invention provides for faster procedure with significantly reduced amount of data being processed and thus allows real-time and accurate inspection of the region of interest.

Those skilled in the art will readily appreciate that various modifications and changes can be applied to the embodiment of the invention as hereinbefore described without departing from its scope defined in and by the appended claims.

The invention claimed is:

1. A monitoring system for use in managing non-invasive inspection of a region of interest on a patient's body to locate a predetermined abnormality, the system being associated with a non-invasive measurement unit for measuring data, the monitoring system comprising:
   a memory utility configured to store reference data comprising: at least one reference response of a body corresponding to a normal condition with respect to at least one abnormality to be detected, and at least one predetermined deviation function corresponding to at least one abnormality to be detected, said at least one predetermined deviation function having a shape characterized by a well-defined global extreme, such that a deviation-related parameter corresponding to the global extreme of the deviation function defines a threshold value for the at least one abnormality to be detected, and a processor utility configured and operable for carrying out the following:
(i) analyzing first measured data including at least two measured data pieces from at least two first spaced-apart measurement locations respectively within a first sub-region of the region of interest and determining for each location a deviation parameter corresponding to deviation of the measured data piece from the reference response with respect to the at least one predetermined abnormality to be detected,
(ii) determining, for each of said at least two of the measured data pieces of the first measured data, a relation between the determined deviation parameter and said deviation-related parameter corresponding to the global extreme of the deviation function, and
(iii) generating a control signal based on the determined relations between the determined deviation parameters and said deviation-related parameter the control signal to the measurement unit, said control signal being indicative of a scan direction towards at least one second location of a second sub-region to be measured in the region of interest where a degree of the at least one abnormality to be detected is higher than in said at least two first locations;
thereby providing a closed loop control of a scan direction towards one or more successive locations in the region of interest with higher degree of abnormality based on the analysis of the measured data from at least two preceding locations, and enabling the inspection to proceed through locations with increasing degree of abnormality while avoiding measurements at locations in the region of interest where a degree of abnormality is relatively low.

2. The system of claim 1, comprising the measurement unit which is configured and operable to measure the data by detecting signals from the measurement locations and to generate the measured data indicative thereof; the measurement unit comprising a control unit configured and operable to be responsive to said control signal from the processor utility and to manage detection of signals from the successive measurements locations spaced from the preceding measured locations along the corresponding scan direction.

3. The system of claim 1, wherein the measured data piece is indicative of a light signal from the corresponding measurement location.

4. The system of claim 3, wherein said light signal is a light response of the corresponding measurement location to incident light.

5. The system of claim 4, wherein the light response comprises at least one of the following: reflected, scattered and excited light portions.

6. The system of claim 5, wherein the processor utility is configured and operable to process at least two different types of the received measured data corresponding to the at least two light responses including at least two of said light portions respectively, thereby enabling identification of more than one abnormality in the region of interest.

7. The system of claim 3, comprising the measurement unit which comprises: an optical system configured and operable to measure the data by detecting light signals from the measurement locations and to generate the measured data indicative thereof; and a control unit configured and operable to be responsive to said control signal from the processor utility for managing detection of the light signals from the successive locations spaced from the previously measured preceding locations along the corresponding scan direction.

8. The system of claim 7, wherein the optical system comprises a light source configured to generate light of multiple wavelengths, and a light detection unit configured to detect the light responses and generate for each light response the respective measured data piece in the form of spectral data.

9. The system of claim 7, wherein the optical system comprises a fiber bundle connected by one end thereof to the light source and the light detector and comprising a plurality of illuminating and detecting optical fibers, said optical system being configured to selectively detect light responses originated at different sets of measurement locations, each set being formed by the at least two spaced-apart locations in the region of interest.

10. The system of claim 9, wherein at least some of the optical fibers are operable as both the illuminating and detecting optical fibers, the control unit being configured and operable to selectively shift said at least some of the optical fibers between illumination and detection modes.

11. The system of claim 9, wherein said measurement unit is configured and operable to controllably vary at least one of illumination and detection light patterns to successively detect light from at least one different measurement location.

12. The system of claim 1, wherein the first measured data comprises data indicative of coordinates of the measurement locations corresponding to the measured data pieces.

13. The system of claim 1, wherein said reference data comprises a library of a plurality of reference responses corresponding to multiple abnormalities of different types, the processor utility being configured to select the reference data to be used for analyzing the received data to detect said at least one abnormality.

14. The system of claim 13, wherein the measured data piece is indicative of a light response of the corresponding measurement location to incident light, the light response comprising at least one of reflected, scattered and excited light portions; the processor utility being configured and operable to process at least two different types of the received measured data corresponding to the at least two light responses including at least two of said light portions respectively, thereby enabling identification of more than one type of abnormality in the region of interest.

15. The system of claim 1, wherein said at least two first spaced-apart locations are spaced from one another by a predetermined distance.

16. The system of claim 1, wherein said at least one second location is spaced from the first sub-region, defined by said at least two first locations, a predetermined distance.

17. The system of claim 1, wherein the processing utility is configured and operable for creating data indicative of a map of variations of the deviation parameter values in said at least two first measurement locations, and analyzing said map to determine a relation between a profile of the variation of the deviation parameter value and a corresponding profile of the deviation function, and thereby determine said scan direction from the first sub-region towards said at least one second location within the second sub-region of the region of interest.

18. A monitoring system for use in managing non-invasive inspection of a region of interest on a patient's body to locate one or more predetermined abnormalities, the system comprising:

an optical measurement unit configured and operable to inspect said region of interest by scanning successive sub-regions of the region of interest, the measurement unit comprising an optical system for applying optical measurements to each sub-region by detecting light from at least two spaced-apart locations within said sub-region;

a memory utility configured to store reference data comprising: at least one reference light response of a body corresponding to a normal condition with respect to at least one abnormality to be detected; and at least one predetermined deviation function corresponding to at least one abnormality to be detected, the deviation function having a shape characterized by a well-defined global extreme, such that a deviation-related parameter corresponding to the global extreme of the deviation function defines a threshold value for the at least one abnormality to be detected;

a processor utility configured and operable for carrying out the following:

(i) analyzing first measured data indicative of the detected light responses from the at least two measurement locations of the first sub-region, and determining for each location a deviation parameter corresponding to deviation of the measured data from the reference light response with respect to the at least one predetermined abnormality to be detected, (ii) determining distribution of a degree of abnormality for said at least one predetermined abnormality in between said at least two measurement locations of the first sub-region, the degree of abnormality being defined by a relation between the determined deviation parameter and said deviation-related parameter corresponding to the global extreme of the deviation function, (iii) determining an optimal scan direction, based on the determined distribution of the degree of abnormality, from the first sub-region towards a second sub-region where the degree of abnormality is higher than in the first sub-region; and (iv) generating a control signal indicative of said optimal scan direction and operating the measurement unit in accordance with said control signal;

repeating steps (i) to (iv) with respect to each successive sub-region, by a closed loop control of the scan direction towards one or more successive sub-regions in the region of interest towards a sub-region with higher degree of abnormality based on the analysis of the measured data from a preceding measured sub-region.

19. The monitoring system of claim 18, wherein the measured data piece is indicative of a light signal from the corresponding measurement location.

20. The monitoring system of claim 19, wherein said light signal is a light response of the corresponding measurement location to incident light, said light response comprising at least one of reflected, scattered, and excited light.

21. A monitoring system for use in managing non-invasive inspection of a region of interest on a patient's body to locate a predetermined abnormality, the system being associated with a non-invasive measurement unit for measuring data and comprising:

a memory utility configured to store reference data comprising: at least one reference response of a body corresponding to a normal condition with respect to at least one abnormality to be detected, and at least one predetermined deviation function corresponding to the at least one abnormality to be detected, said at least one predetermined deviation function having a shape characterized by a well-defined global extreme, such that a deviation-related parameter corresponding to the global extreme of the deviation function defines a threshold value for the at least one abnormality to be detected, and a processor utility configured and operable for carrying out the following:

(i) analyzing first measured data including at least two measured data pieces from at least two first spaced-apart measurement locations respectively within a first sub-region of the region of interest and determining for each location a deviation parameter corresponding to deviation of the measured data piece from the reference response with respect to the at least one predetermined abnormality to be detected;

(ii) determining, for each of said at least two of the measured data pieces of the first measured data, a relation between the determined deviation parameter and said deviation-related parameter corresponding to the global extreme of the deviation function, (iii) creating data indicative of a map of variations of the determined deviation parameter values in said at least two first measurement locations, based on the determined relations between the determined deviation parameters and said deviation-related parameter, and analyzing said map to determine a relation between a profile of the variation of the determined deviation parameter values and a corresponding profile of the deviation function, and based on the relation between the variation of the determined deviation parameter values and the corresponding profile of the deviation function, determining a scan direction towards at least one second location of a second sub-region to be measured in the region of interest where a degree of the at least one abnormality to be detected is higher than in said at least two first locations, and (iv) generating a control signal indicative of said scan direction and communicating the control signal to the measurement unit;

thereby providing a closed loop control of a scan direction towards one or more successive locations in the region of interest with higher degree of abnormality based on the analysis of the measured data from at least two preceding locations, and enabling the inspection to proceed through locations with increasing degree of abnormality while avoiding measurements at locations in the region of interest where a degree of abnormality is relatively low.

* * * * *